United States Patent
Ratz et al.

(10) Patent No.: US 12,083,011 B2
(45) Date of Patent: Sep. 10, 2024

(54) REPLACEMENT HEART VALVE

(71) Applicant: Edwards Lifesciences CardiAQ LLC, Irvine, CA (US)

(72) Inventors: Jeremy Brent Ratz, Winchester, MA (US); Luca Pesce, Huntington Beach, CA (US); Glen T. Rabito, Lake Forest, CA (US); Christine Thanh Nguyen, Santa Ana, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 206 days.

(21) Appl. No.: 17/357,816

(22) Filed: Jun. 24, 2021

(65) Prior Publication Data

US 2021/0315692 A1    Oct. 14, 2021

Related U.S. Application Data

(63) Continuation of application No. 16/247,403, filed on Jan. 14, 2019, now Pat. No. 11,045,313, which is a
(Continued)

(51) Int. Cl.
| | |
|---|---|
| *A61F 2/24* | (2006.01) |
| *A61L 27/04* | (2006.01) |
| *A61L 27/36* | (2006.01) |

(52) U.S. Cl.
CPC .......... *A61F 2/2418* (2013.01); *A61F 2/2445* (2013.01); *A61F 2220/0008* (2013.01);
(Continued)

(58) Field of Classification Search
None
See application file for complete search history.

(56) References Cited

U.S. PATENT DOCUMENTS

| | | |
|---|---|---|
| 3,657,744 A | 4/1972 | Ersek |
| 3,671,979 A | 6/1972 | Moulopoulos |

(Continued)

FOREIGN PATENT DOCUMENTS

| | | |
|---|---|---|
| CA | 2304325 A1 | 10/2000 |
| CA | 2827556 A1 | 7/2012 |

(Continued)

OTHER PUBLICATIONS

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as June of 2014.
(Continued)

*Primary Examiner* — Ann Schillinger
(74) *Attorney, Agent, or Firm* — Thomas Richardson

(57) ABSTRACT

A prosthesis for placement within a native heart valve preferably includes an expandable frame having locking tabs disposed along a proximal end. A plurality of distal anchors is disposed along a distal end of the frame. Each distal anchor is provided with a cushion cover. An outer fabric member surrounds the frame and may extend outwardly from the frame in an expanded condition for providing an improved seal in the region of a native annulus. A valve body is positioned within an interior of the expandable from for allowing blood flow in only one direction. In preferred embodiments, the cushions are positioned over enlarged head portions of the distal anchors for further reducing trauma on surrounding tissue.

17 Claims, 17 Drawing Sheets

Related U.S. Application Data continuation of application No. 15/462,438, filed on Mar. 17, 2017, now Pat. No. 10,179,044, which is a continuation of application No. 14/716,507, filed on May 19, 2015, now abandoned.

(60) Provisional application No. 62/000,309, filed on May 19, 2014.

(52) U.S. Cl.
CPC ............... *A61F 2220/005* (2013.01); *A61F 2220/0075* (2013.01); *A61F 2250/0039* (2013.01); *A61F 2250/0069* (2013.01)

(56) References Cited

U.S. PATENT DOCUMENTS

| | | | |
|---|---|---|---|
| 3,739,402 | A | 6/1973 | Cooley et al. |
| 4,056,854 | A | 11/1977 | Boretos et al. |
| 4,079,468 | A | 3/1978 | Liotta et al. |
| 4,204,283 | A | 5/1980 | Bellhouse et al. |
| 4,222,126 | A | 9/1980 | Boretos et al. |
| 4,265,694 | A | 5/1981 | Boretos et al. |
| 4,339,831 | A | 7/1982 | Johnson |
| 4,340,977 | A | 7/1982 | Brownlee et al. |
| 4,470,157 | A | 9/1984 | Love |
| 4,477,930 | A | 10/1984 | Totten et al. |
| 4,490,859 | A | 1/1985 | Black et al. |
| 4,553,545 | A | 11/1985 | Maass et al. |
| 4,777,951 | A | 10/1988 | Cribier et al. |
| 4,865,600 | A | 9/1989 | Carpentier et al. |
| 4,994,077 | A | 2/1991 | Dobben |
| 5,326,371 | A | 7/1994 | Love et al. |
| 5,332,402 | A | 7/1994 | Teitelbaum |
| 5,370,685 | A | 12/1994 | Stevens |
| 5,411,552 | A | 5/1995 | Andersen et al. |
| 5,415,667 | A | 5/1995 | Frater |
| 5,545,214 | A | 8/1996 | Stevens |
| 5,554,185 | A | 9/1996 | Block et al. |
| 5,697,382 | A | 12/1997 | Love et al. |
| 5,840,081 | A | 11/1998 | Andersen et al. |
| 5,855,601 | A | 1/1999 | Bessler et al. |
| 5,957,949 | A | 9/1999 | Leonhardt et al. |
| 6,086,612 | A | 7/2000 | Jansen |
| 6,113,631 | A | 9/2000 | Jansen |
| 6,168,614 | B1 | 1/2001 | Andersen et al. |
| 6,251,093 | B1 | 6/2001 | Valley et al. |
| 6,312,465 | B1 | 11/2001 | Griffin et al. |
| 6,358,277 | B1 | 3/2002 | Duran |
| 6,440,164 | B1 | 8/2002 | DiMatteo et al. |
| 6,458,153 | B1 | 10/2002 | Bailey et al. |
| 6,482,228 | B1 | 11/2002 | Norred |
| 6,527,800 | B1 | 3/2003 | McGuckin, Jr. et al. |
| 6,582,462 | B1 | 6/2003 | Andersen et al. |
| 6,610,088 | B1 | 8/2003 | Gabbay |
| 6,629,534 | B1 | 10/2003 | St. Goar et al. |
| 6,652,578 | B2 | 11/2003 | Bailey et al. |
| 6,676,698 | B2 | 1/2004 | McGuckin, Jr. et al. |
| 6,695,878 | B2 | 2/2004 | McGuckin, Jr. et al. |
| 6,712,836 | B1 * | 3/2004 | Berg ............... A61B 17/0057 |
| | | | 606/213 |
| 6,716,207 | B2 | 4/2004 | Farnholtz |
| 6,729,356 | B1 | 5/2004 | Baker et al. |
| 6,730,118 | B2 | 5/2004 | Spenser et al. |
| 6,746,422 | B1 | 6/2004 | Noriega et al. |
| 6,749,560 | B1 | 6/2004 | Konstorum et al. |
| 6,767,362 | B2 | 7/2004 | Schreck |
| 6,780,200 | B2 | 8/2004 | Jansen |
| 6,790,229 | B1 | 9/2004 | Berreklouw |
| 6,790,230 | B2 | 9/2004 | Beyersdorf et al. |
| 6,875,231 | B2 | 4/2005 | Anduiza et al. |
| 6,893,460 | B2 | 5/2005 | Spenser et al. |
| 6,908,481 | B2 | 6/2005 | Cribier |
| 7,186,265 | B2 | 3/2007 | Sharkawy et al. |
| 7,192,440 | B2 | 3/2007 | Andreas et al. |
| 7,198,646 | B2 | 4/2007 | Figulla et al. |
| 7,201,772 | B2 | 4/2007 | Schwammenthal et al. |
| 7,276,078 | B2 | 10/2007 | Spenser et al. |
| 7,393,360 | B2 | 7/2008 | Spenser et al. |
| 7,429,269 | B2 | 9/2008 | Schwammenthal et al. |
| 7,442,204 | B2 | 10/2008 | Schwammenthal et al. |
| 7,462,191 | B2 | 12/2008 | Spenser et al. |
| 7,510,575 | B2 | 3/2009 | Spenser et al. |
| 7,524,330 | B2 | 4/2009 | Berreklouw |
| 7,553,324 | B2 | 6/2009 | Andreas et al. |
| 7,585,321 | B2 | 9/2009 | Cribier |
| 7,618,446 | B2 | 11/2009 | Andersen et al. |
| 7,621,948 | B2 | 11/2009 | Herrmann et al. |
| 7,628,805 | B2 | 12/2009 | Spenser et al. |
| 7,753,949 | B2 | 7/2010 | Amphere et al. |
| 7,803,185 | B2 | 9/2010 | Gabbay |
| 7,806,919 | B2 | 10/2010 | Bloom et al. |
| 7,815,673 | B2 | 10/2010 | Bloom et al. |
| 7,914,569 | B2 | 3/2011 | Nguyen et al. |
| 7,947,075 | B2 | 5/2011 | Goetz et al. |
| 7,972,378 | B2 | 7/2011 | Tabor et al. |
| 7,981,151 | B2 | 7/2011 | Rowe |
| 7,993,392 | B2 | 8/2011 | Righini et al. |
| 8,043,360 | B2 * | 10/2011 | McNamara ............ A61B 17/11 |
| | | | 623/1.15 |
| 8,070,800 | B2 | 12/2011 | Lock et al. |
| 8,070,802 | B2 | 12/2011 | Lamphere et al. |
| 8,075,615 | B2 | 12/2011 | Eberhardt et al. |
| 8,080,054 | B2 | 12/2011 | Rowe |
| 8,092,520 | B2 | 1/2012 | Quadri |
| 8,109,996 | B2 | 2/2012 | Stacchino et al. |
| 8,118,866 | B2 | 2/2012 | Herrmann et al. |
| 8,136,218 | B2 | 3/2012 | Millwee et al. |
| 8,137,398 | B2 | 3/2012 | Tuval et al. |
| 8,157,852 | B2 | 4/2012 | Bloom et al. |
| 8,167,934 | B2 | 5/2012 | Styrc et al. |
| 8,182,530 | B2 | 5/2012 | Huber |
| 8,216,301 | B2 | 7/2012 | Bonhoeffer et al. |
| 8,219,229 | B2 | 7/2012 | Cao et al. |
| 8,220,121 | B2 | 7/2012 | Hendriksen et al. |
| 8,221,493 | B2 | 7/2012 | Boyle et al. |
| 8,226,710 | B2 | 7/2012 | Nguyen et al. |
| 8,236,045 | B2 | 8/2012 | Benichou et al. |
| 8,246,675 | B2 | 8/2012 | Zegdi |
| 8,252,051 | B2 | 8/2012 | Chau et al. |
| 8,303,653 | B2 | 11/2012 | Bonhoeffer et al. |
| 8,313,525 | B2 | 11/2012 | Tuval et al. |
| 8,323,335 | B2 | 12/2012 | Rowe et al. |
| 8,353,953 | B2 | 1/2013 | Giannetti et al. |
| 8,414,645 | B2 | 4/2013 | Dwork et al. |
| 8,444,689 | B2 | 5/2013 | Zhang |
| 8,449,599 | B2 | 5/2013 | Chau et al. |
| 8,454,685 | B2 | 6/2013 | Hariton et al. |
| 8,460,368 | B2 | 6/2013 | Taylor et al. |
| 8,470,023 | B2 | 6/2013 | Eidenschink et al. |
| 8,475,521 | B2 | 7/2013 | Suri et al. |
| 8,475,523 | B2 | 7/2013 | Duffy |
| 8,479,380 | B2 | 7/2013 | Malewicz et al. |
| 8,486,137 | B2 | 7/2013 | Suri et al. |
| 8,491,650 | B2 | 7/2013 | Wiemeyer et al. |
| 8,500,733 | B2 | 8/2013 | Watson |
| 8,500,798 | B2 | 8/2013 | Rowe et al. |
| 8,511,244 | B2 | 8/2013 | Holecek et al. |
| 8,512,401 | B2 | 8/2013 | Murray, III et al. |
| 8,518,096 | B2 | 8/2013 | Nelson |
| 8,518,106 | B2 | 8/2013 | Duffy et al. |
| 8,562,663 | B2 | 10/2013 | Mearns et al. |
| 8,579,963 | B2 | 11/2013 | Tabor |
| 8,579,964 | B2 | 11/2013 | Lane et al. |
| 8,579,965 | B2 | 11/2013 | Bonhoeffer et al. |
| 8,585,755 | B2 | 11/2013 | Chau et al. |
| 8,585,756 | B2 | 11/2013 | Bonhoeffer et al. |
| 8,591,570 | B2 | 11/2013 | Revuelta et al. |
| 8,597,348 | B2 | 12/2013 | Rowe et al. |
| 8,640,521 | B2 | 2/2014 | Righini et al. |
| 8,647,381 | B2 | 2/2014 | Essinger et al. |
| 8,652,145 | B2 | 2/2014 | Maimon et al. |
| 8,652,201 | B2 | 2/2014 | Oberti et al. |
| 8,652,202 | B2 | 2/2014 | Alon et al. |

(56) References Cited

U.S. PATENT DOCUMENTS

| | | | |
|---|---|---|---|
| 8,673,000 B2 | 3/2014 | Tabor et al. | |
| 8,679,174 B2 | 3/2014 | Ottma et al. | |
| 8,679,404 B2 | 3/2014 | Liburd et al. | |
| 8,685,086 B2* | 4/2014 | Navia | A61F 2/2418 623/2.14 |
| 8,721,714 B2 | 5/2014 | Kelley | |
| 8,728,154 B2 | 5/2014 | Alkhatib | |
| 8,728,155 B2 | 5/2014 | Montorfano et al. | |
| 8,740,974 B2 | 6/2014 | Lambrecht et al. | |
| 8,740,976 B2 | 6/2014 | Tran et al. | |
| 8,747,458 B2 | 6/2014 | Tuval et al. | |
| 8,747,459 B2 | 6/2014 | Nguyen et al. | |
| 8,764,818 B2 | 7/2014 | Gregg | |
| 8,771,344 B2 | 7/2014 | Tran et al. | |
| 8,778,020 B2 | 7/2014 | Gregg et al. | |
| 8,784,337 B2 | 7/2014 | Voeller et al. | |
| 8,784,478 B2 | 7/2014 | Tuval et al. | |
| 8,784,481 B2 | 7/2014 | Alkhatib et al. | |
| 8,790,387 B2 | 7/2014 | Nguyen et al. | |
| 8,795,357 B2 | 8/2014 | Yohanan et al. | |
| 8,808,356 B2 | 8/2014 | Braido et al. | |
| 8,828,079 B2 | 9/2014 | Thielen et al. | |
| 8,845,718 B2 | 9/2014 | Tuval et al. | |
| 8,858,620 B2 | 10/2014 | Salahieh et al. | |
| 8,870,948 B1 | 10/2014 | Erzberger et al. | |
| 8,870,950 B2 | 10/2014 | Hacohen | |
| 8,876,893 B2 | 11/2014 | Dwork et al. | |
| 8,911,455 B2 | 12/2014 | Quadri et al. | |
| 8,926,693 B2 | 1/2015 | Duffy et al. | |
| 8,926,694 B2 | 1/2015 | Costello | |
| 8,939,960 B2 | 1/2015 | Rosenman et al. | |
| 8,945,209 B2 | 2/2015 | Bonyuet et al. | |
| 8,961,593 B2 | 2/2015 | Bonhoeffer et al. | |
| 8,961,595 B2 | 2/2015 | Alkhatib | |
| 8,974,524 B2 | 3/2015 | Yeung et al. | |
| 8,979,922 B2 | 3/2015 | Jayasinghe et al. | |
| 8,986,372 B2 | 3/2015 | Murry, III et al. | |
| 8,986,375 B2 | 3/2015 | Garde et al. | |
| 8,992,604 B2* | 3/2015 | Gross | A61F 2/2412 623/2.11 |
| 8,998,980 B2 | 4/2015 | Shipley et al. | |
| 9,011,523 B2 | 4/2015 | Seguin | |
| 9,011,524 B2 | 4/2015 | Eberhardt | |
| 9,028,545 B2 | 5/2015 | Taylor | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,055,937 B2 | 6/2015 | Rowe et al. | |
| 9,066,801 B2 | 6/2015 | Kovalsky et al. | |
| 9,078,751 B2 | 7/2015 | Naor | |
| 9,084,676 B2 | 7/2015 | Chau et al. | |
| 9,125,738 B2* | 9/2015 | Figulla | A61F 2/2418 |
| 9,125,740 B2* | 9/2015 | Morriss | A61F 2/2445 |
| 9,161,834 B2 | 10/2015 | Taylor et al. | |
| 9,173,737 B2 | 11/2015 | Hill et al. | |
| 9,180,004 B2 | 11/2015 | Alkhatib | |
| 9,186,249 B2 | 11/2015 | Rolando et al. | |
| 9,220,594 B2 | 12/2015 | Braido et al. | |
| 9,241,790 B2 | 1/2016 | Lane et al. | |
| 9,248,014 B2 | 2/2016 | Lane et al. | |
| 9,277,990 B2 | 3/2016 | Klima et al. | |
| 9,277,993 B2 | 3/2016 | Gamarra et al. | |
| 9,289,291 B2 | 3/2016 | Gorman, III et al. | |
| 9,289,296 B2 | 3/2016 | Braido et al. | |
| 9,295,551 B2 | 3/2016 | Straubinger et al. | |
| 9,326,815 B2 | 5/2016 | Watson | |
| 9,331,328 B2 | 5/2016 | Eberhardt et al. | |
| 9,339,382 B2 | 5/2016 | Tabor et al. | |
| 9,351,831 B2 | 5/2016 | Braido et al. | |
| 9,351,832 B2 | 5/2016 | Braido et al. | |
| 9,364,321 B2 | 6/2016 | Alkhatib et al. | |
| 9,445,897 B2 | 9/2016 | Bishop et al. | |
| 9,456,877 B2 | 10/2016 | Weitzner et al. | |
| 9,681,968 B2 | 6/2017 | Goetz et al. | |
| 9,700,329 B2 | 7/2017 | Metzger et al. | |
| 9,700,411 B2 | 7/2017 | Klima et al. | |
| 9,795,479 B2 | 10/2017 | Lim et al. | |
| 9,833,313 B2 | 12/2017 | Board et al. | |
| 9,861,473 B2 | 1/2018 | Lafontaine | |
| 9,861,476 B2 | 1/2018 | Salahieh et al. | |
| 9,861,477 B2 | 1/2018 | Backus et al. | |
| 9,867,698 B2 | 1/2018 | Kovalsky et al. | |
| 9,877,830 B2 | 1/2018 | Lim et al. | |
| 9,889,029 B2 | 2/2018 | Li et al. | |
| 9,895,225 B2 | 2/2018 | Rolando et al. | |
| 9,925,045 B2 | 3/2018 | Creaven et al. | |
| 10,179,044 B2 | 1/2019 | Ratz et al. | |
| 10,639,143 B2* | 5/2020 | Oba | A61L 27/04 |
| 2001/0007956 A1 | 7/2001 | Letac et al. | |
| 2002/0016623 A1 | 2/2002 | Kula et al. | |
| 2002/0032481 A1 | 3/2002 | Gabbay | |
| 2002/0045929 A1 | 4/2002 | Diaz | |
| 2002/0052644 A1 | 5/2002 | Shaolian et al. | |
| 2003/0105517 A1 | 6/2003 | White et al. | |
| 2003/0120333 A1 | 6/2003 | Ouriel et al. | |
| 2003/0130729 A1 | 7/2003 | Paniagua et al. | |
| 2003/0176914 A1 | 9/2003 | Rabkin et al. | |
| 2003/0199971 A1 | 10/2003 | Tower et al. | |
| 2003/0220683 A1 | 11/2003 | Minasian et al. | |
| 2004/0117009 A1 | 6/2004 | Cali et al. | |
| 2004/0133273 A1 | 7/2004 | Cox | |
| 2004/0186561 A1 | 9/2004 | McGuckin et al. | |
| 2004/0210307 A1 | 10/2004 | Khairkhahan | |
| 2004/0215325 A1 | 10/2004 | Penn et al. | |
| 2004/0236411 A1 | 11/2004 | Sarac et al. | |
| 2005/0033398 A1 | 2/2005 | Seguin | |
| 2005/0075727 A1 | 4/2005 | Wheatley | |
| 2005/0090887 A1 | 4/2005 | Pryor | |
| 2005/0096738 A1 | 5/2005 | Cali et al. | |
| 2005/0107872 A1 | 5/2005 | Mensah et al. | |
| 2005/0137682 A1 | 6/2005 | Justino | |
| 2005/0137690 A1* | 6/2005 | Salahieh | A61F 2/2427 623/1.36 |
| 2005/0137691 A1* | 6/2005 | Salahieh | A61F 2/2418 623/2.11 |
| 2005/0159811 A1 | 7/2005 | Lane | |
| 2005/0182486 A1 | 8/2005 | Gabbay | |
| 2005/0216079 A1 | 9/2005 | MaCoviak | |
| 2005/0234546 A1 | 10/2005 | Nugent et al. | |
| 2006/0020327 A1 | 1/2006 | Lashinski et al. | |
| 2006/0052867 A1 | 3/2006 | Revuelta et al. | |
| 2006/0095115 A1 | 5/2006 | Bladillah et al. | |
| 2006/0173537 A1 | 8/2006 | Yang et al. | |
| 2006/0195183 A1* | 8/2006 | Navia | A61F 2/2418 623/2.11 |
| 2006/0212110 A1 | 9/2006 | Osborne et al. | |
| 2006/0259135 A1 | 11/2006 | Navia et al. | |
| 2006/0259136 A1 | 11/2006 | Nguyen et al. | |
| 2006/0265056 A1 | 11/2006 | Nguyen et al. | |
| 2006/0287717 A1 | 12/2006 | Rowe et al. | |
| 2006/0293745 A1 | 12/2006 | Carpentier et al. | |
| 2007/0050021 A1 | 3/2007 | Johnson | |
| 2007/0100432 A1 | 5/2007 | Case et al. | |
| 2007/0129794 A1 | 6/2007 | Realyvasquez | |
| 2007/0142906 A1 | 6/2007 | Figulla et al. | |
| 2007/0213813 A1 | 9/2007 | Von Segesser et al. | |
| 2007/0255394 A1 | 11/2007 | Ryan | |
| 2007/0293944 A1* | 12/2007 | Spenser | A61F 2/2409 623/2.11 |
| 2008/0021546 A1 | 1/2008 | Patz et al. | |
| 2008/0082164 A1 | 4/2008 | Friedman | |
| 2008/0082165 A1 | 4/2008 | Wilson et al. | |
| 2008/0097581 A1 | 4/2008 | Shanley | |
| 2008/0147179 A1 | 6/2008 | Cai et al. | |
| 2008/0147183 A1 | 6/2008 | Styrc | |
| 2008/0161911 A1 | 7/2008 | Revuelta et al. | |
| 2008/0177381 A1* | 7/2008 | Navia | A61F 2/2433 623/2.11 |
| 2008/0183273 A1 | 7/2008 | Mesana et al. | |
| 2008/0208328 A1 | 8/2008 | Antocci et al. | |
| 2008/0228254 A1 | 9/2008 | Ryan | |
| 2009/0005863 A1* | 1/2009 | Goetz | A61F 2/2418 623/2.18 |
| 2009/0138079 A1 | 5/2009 | Tuval et al. | |

(56) References Cited

U.S. PATENT DOCUMENTS

| | | |
|---|---|---|
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0287299 A1* | 11/2009 | Tabor ................ A61F 2/07 623/1.26 |
| 2009/0292350 A1 | 11/2009 | Eberhardt et al. |
| 2009/0306768 A1 | 12/2009 | Quadri |
| 2010/0114305 A1 | 5/2010 | Kang et al. |
| 2010/0121423 A1 | 5/2010 | Bernhard et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2010/0312333 A1* | 12/2010 | Navia ............... A61F 2/2418 623/2.36 |
| 2011/0029067 A1 | 2/2011 | McGuckin, Jr. et al. |
| 2011/0029072 A1* | 2/2011 | Gabbay ............. A61F 2/2418 623/2.37 |
| 2011/0137397 A1* | 6/2011 | Chau .................. A61F 2/246 623/2.37 |
| 2011/0208297 A1 | 8/2011 | Tuval et al. |
| 2011/0208298 A1 | 8/2011 | Tuval et al. |
| 2011/0224785 A1* | 9/2011 | Hacohen ........... A61F 2/2457 623/2.18 |
| 2011/0264196 A1 | 10/2011 | Savage et al. |
| 2012/0022633 A1 | 1/2012 | Olson et al. |
| 2012/0022639 A1 | 1/2012 | Hacohen et al. |
| 2012/0059454 A1 | 3/2012 | Millwee et al. |
| 2012/0078360 A1* | 3/2012 | Rafiee ............... A61F 2/2418 623/2.37 |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0303116 A1* | 11/2012 | Gorman, III ....... A61F 2/2436 623/2.11 |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0274873 A1 | 10/2013 | Delaloye et al. |
| 2013/0310928 A1* | 11/2013 | Morriss ............. A61F 2/2409 623/2.18 |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0025164 A1* | 1/2014 | Montorfano ...... A61F 2/2418 623/2.37 |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0155997 A1* | 6/2014 | Braido .............. A61F 2/2418 623/2.37 |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1* | 8/2014 | Geist ................ A61F 2/2412 623/2.37 |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1* | 9/2014 | Ratz ................. A61F 2/2409 623/2.38 |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309732 A1 | 10/2014 | Solem |
| 2014/0324160 A1 | 10/2014 | Benichou et al. |
| 2014/0324164 A1* | 10/2014 | Gross ............... A61F 2/2418 623/2.37 |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1* | 12/2014 | Dale ................. A61F 2/2436 623/2.11 |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2015/0005863 A1 | 1/2015 | Para |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | Mcnamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1* | 2/2016 | Alkhatib ........... A61F 2/2418 623/2.17 |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |

(56) References Cited

U.S. PATENT DOCUMENTS

| | | | |
|---|---|---|---|
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| CN | 102869319 A | 1/2013 |
| DE | 102006052564 B3 | 12/2007 |
| EP | 1171059 A1 | 1/2002 |
| EP | 1369098 A1 | 12/2003 |
| EP | 1472996 A1 | 11/2004 |
| EP | 1259194 B1 | 2/2005 |
| EP | 1734903 A1 | 12/2006 |
| EP | 1255510 B1 | 4/2007 |
| EP | 1827558 A2 | 9/2007 |
| EP | 1239901 B1 | 10/2007 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2398543 A1 | 12/2011 |
| EP | 1281375 B1 | 2/2012 |
| EP | 2496182 A1 | 9/2012 |
| EP | 2566416 A1 | 3/2013 |
| EP | 2319458 B1 | 4/2013 |
| EP | 2124826 B1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2967858 A2 | 1/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| NO | 2010057262 A1 | 5/2010 |
| NO | 2011025945 A1 | 3/2011 |
| WO | 9749355 A1 | 12/1997 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010040009 A1 | 4/2010 |
| WO | 2011057087 A1 | 5/2011 |
| WO | 2011111047 A2 | 9/2011 |
| WO | 2011137531 A1 | 11/2011 |
| WO | 2012095159 A2 | 7/2012 |
| WO | 2012177942 A2 | 12/2012 |
| WO | 2013028387 A2 | 2/2013 |
| WO | 2013059747 A1 | 4/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014/022124 | 2/2014 |
| WO | 2014022124 A1 | 2/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Bavaria, Joseph E. M.D. et al.: "Transcatheter Mitral Valve Implantation: The Future Gold Standard for MR?," Applicant requests the Examiner to consider this reference to be prior art as of December of 2010.

Bavaria, Joseph E. M.D.: "CardiAQ Valve Technologies: Transcatheter Mitral Valve Implantation," Sep. 21, 2009.

Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

Boudjemline, Younes, et al., "Steps Toward the Percutaneous Replacement of Atrioventricular Valves," JACC, vol. 46, No. 2, Jul. 19, 2005:360-5.

(56) References Cited

OTHER PUBLICATIONS

"CardiAQTM Valve Technologies reports Successful First-in-Human Trans-Apical implantation of its Second Generation Transcatheter Mitral Valve," CardiAQ Valve Technologies Press Release, May 20, 2014.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
"Company Overview," at TVT on Jun. 25, 2009.
Condado, Jose Antonio, et al., "Percutaneous Treatment of Heart Valves," Rev Esp Cardio. 2006;59(12):1225-31, Applicant believes this may have been available as early as Dec. of 2006.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Fanning, Jonathon P., et al., "Transcatheter Aortic Valve Implantation (TAVI): Valve Design And Evolution," International Journal of Cardiology 168 (2013) 1822-1831, Applicant believes this may have been available as early as Oct. 3, 2013.
Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Feldman, Ted, MD. "Prospects for Percutaneous Valve Therapies," Circulation 2007;116:2866-2877. Applicant believes that this may be available as early as Dec. 11, 2007.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Spillner, J. et al., "New Sutureless 'Atrial-Mitral-Valve Prosthesis' For Minimally Invasive Mitral Valve Therapy," Textile Research Journal, 2010, in 7 pages, Applicant believes this may have been available as early as Aug. 9, 2010.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Ma, Liang, et al., "Double-Crowned Valved Stents For Off-Pump Mitral Valve Replacement," European Journal of Cardio-thoracic Surgery 28 (2005) 194-199, Applicant believes this may have been available as early as August of 2005.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Mack, Michael, M.D., "Antegrade Transcatheter Mitral valve Implantation: On-Going Experience in Swine Model," Applicant believes this may have been presented on November of 2011 at TCT.
Mack, Michael, M.D., "Antegrade Transcatheter Mitral valve Implantation: A Short-term Experience in Swine Model," Applicant believes this may have been presented on May of 2011 at TVT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as August of 2008.
Pluth, James R., M.D., et al., "Aortic and Mitral Valve Replacement with Cloth-Covered Braunwald-Cutter Prosthesis, A Three-Year Follow-up," The Annals Of Thoracic Surgery, vol. 20, No. 3, Sep. 1975, pp. 239-248.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "LSI EMT Spotlight," May 15, 2009.
Ratz, J. Brent, "In3 Company Overview," Jun. 24, 2009.
Ruiz, Carlos E., "Overview of Novel Transcatheter Valve Technologies," Applicant believes this may have been presented on May 27, 2010 at EuroPCR.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/hrcardio/journal/v11/n3/full/nrcardio.2013.221.html?message-global=remove#access. Jan. 21, 2014.

(56) References Cited

OTHER PUBLICATIONS

"Update," Applicant believes this may have been presented on Jun. 6, 2010 at TVT.

Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).

Vu, Duc-Thang, et al., "Novel Sutureless Mitral Valve Implantation Method Involving A Bayonet Insertion And Release Mechanism: A Proof Of Concept Study In Pigs," The Journal of Thoracic and Cardiovascular Surgery, vol. 143, No. 4, 985-988, Apr. 2012, Applicant believes this may have been available online as early as Feb. 13, 2012.

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

Webb, John G., et al., "Transcatheter Aortic Valve Implantation: The Evolution Of Prostheses, Delivery Systems And Approaches," Archives of Cardiovascular Disease (2012) 105, 153-159. Applicant believes this may have been available as early as Mar. 16, 2012.

\* cited by examiner

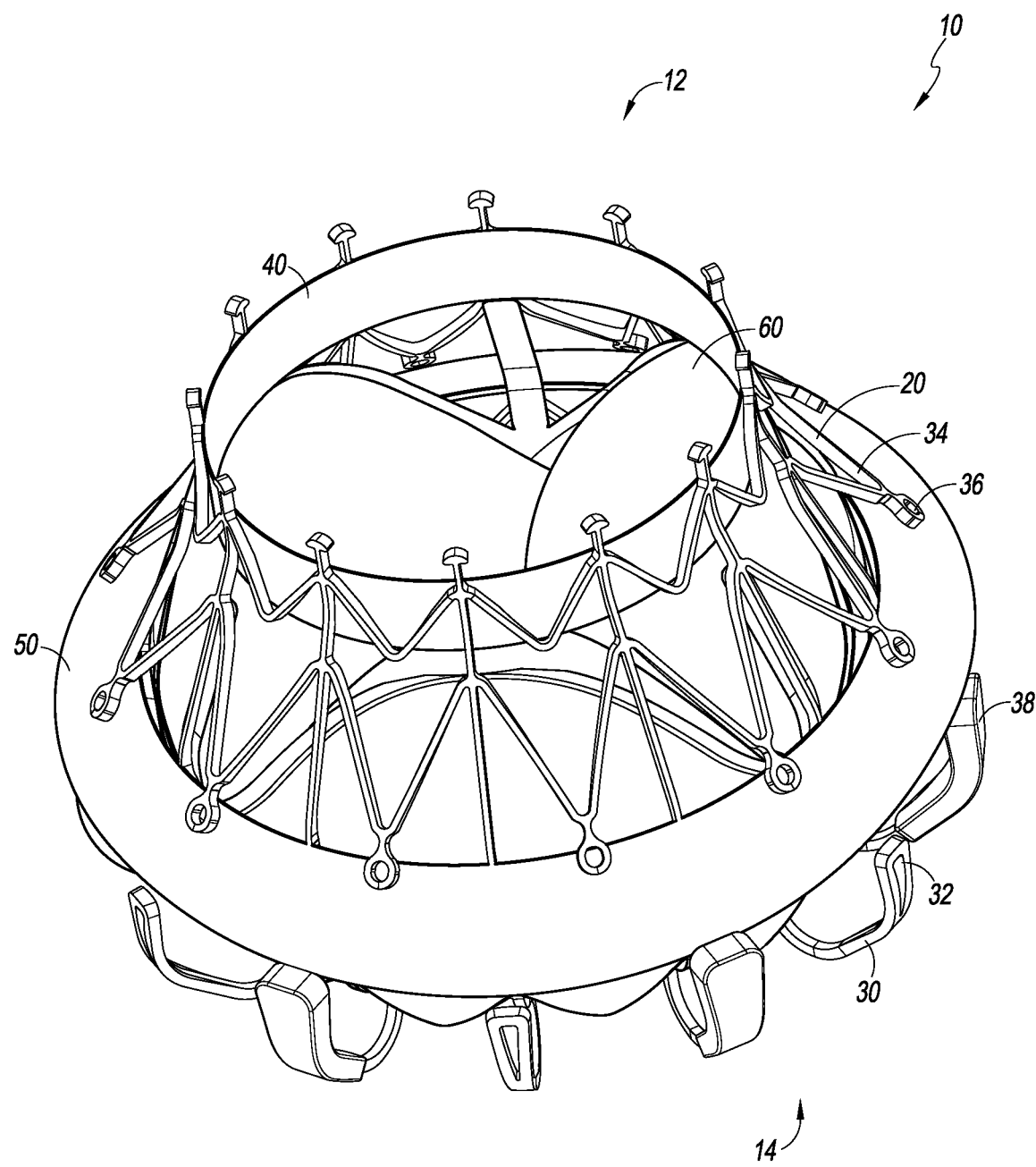
FIG. IA

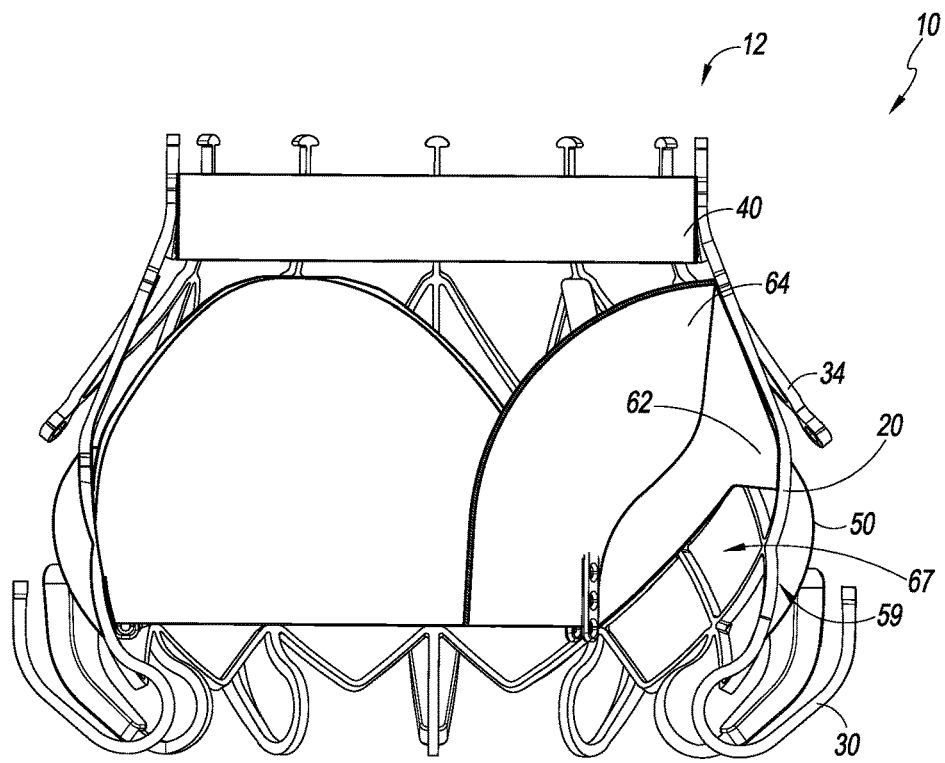
FIG. IIA
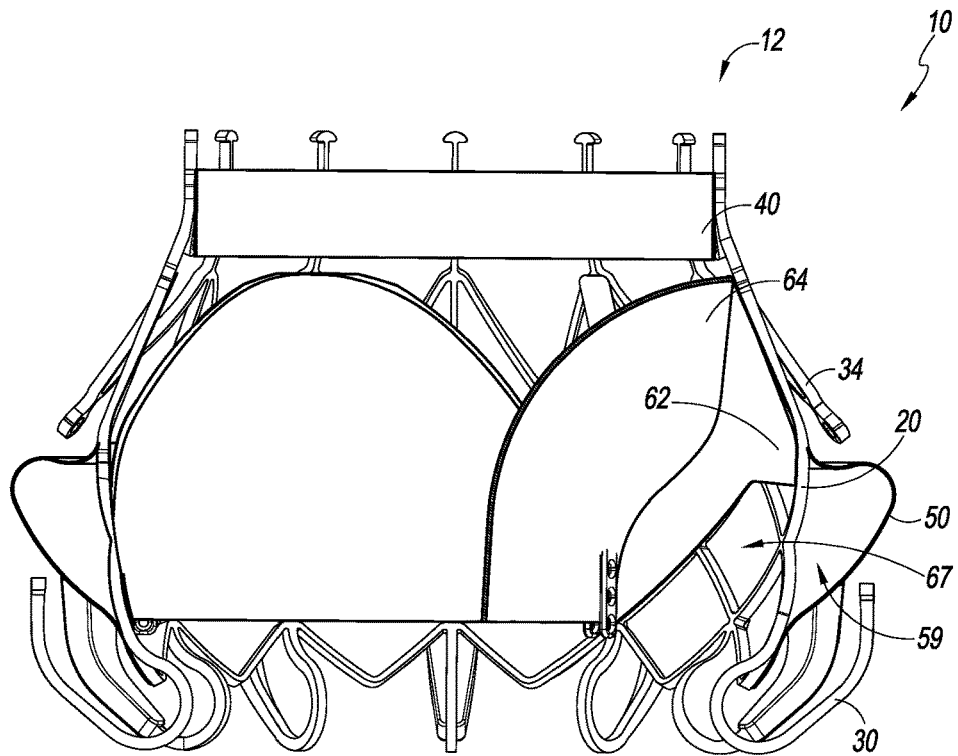
FIG. IIB

REPLACEMENT HEART VALVE

CROSS-REFERENCE TO RELATED APPLICATIONS

This application is a continuation of U.S. application Ser. No. 16/247,403, filed Jan. 14, 2019, now U.S. Pat. No. 11,045,313, which is a continuation of U.S. application Ser. No. 15/462,438, filed Mar. 17, 2017, now U.S. Pat. No. 10,179,044, which is a continuation of U.S. application Ser. No. 14/716,507, filed May 19, 2015, now abandoned, which claims priority to U.S. Provisional Application No. 62/000,309 filed May 19, 2014, which is hereby incorporated herein by reference in its entirety and is to be considered a part of this specification.

BACKGROUND

Field

Certain embodiments disclosed herein relate generally to prostheses for implantation within a lumen or body cavity. In particular, certain embodiments relate to expandable prostheses such as replacement heart valves, such as for the mitral valve, that are configured to atraumatically grasp intralumenal tissue.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

These replacement valves are often intended to at least partially block blood flow. However, a problem occurs when blood flows around the valve on the outside of the prosthesis. For example, in the context of replacement heart valves, paravalvular leakage has proven particularly challenging. An additional challenge relates to the ability of such prostheses to be secured relative to intralumenal tissue, e.g., tissue within any body lumen or cavity, in an atraumatic manner. Further challenges arise when trying to controllably deliver and secure such prostheses in a location such as at a native mitral valve.

SUMMARY OF THE INVENTION

Embodiments of the present disclosure are directed to a prosthesis, such as but not limited to a replacement heart valve. According to some embodiments, a prosthesis can be configured to be deployed within a body cavity and prevent axial flow of fluid around an exterior of the prosthesis. The prosthesis can include an expandable frame configured to radially expand and contract for deployment within the body cavity, and an annular flap positioned around an exterior of the expandable frame. Further embodiments are directed to methods of delivering a prosthesis, e.g. a replacement heart valve, and methods of using a prosthesis to create a barrier to fluid flow exterior to the prosthesis (e.g., to prevent paravalvular leakage).

In some embodiments, the prosthesis can include an expandable frame having a proximal end and a distal end and a longitudinal axis extending therethrough. In some embodiments, the frame can be designed to radially expand and contract for deployment within the body cavity. The prosthesis can include an annular flap positioned around and secured to an exterior of the frame. The annular flap may have a distal edge secured at or near the distal end of the frame and extending to a proximal edge secured at an intermediate location on the frame between the proximal and distal ends. The prosthesis can include a valve body positioned within an interior of the expandable frame. In some embodiments, the valve body can include an inner skirt secured to the interior of the expandable frame and a plurality of leaflets designed to allow flow in a first direction and prevent flow in a second opposite direction. In some embodiments, an opening is defined at or near the distal end of the frame between the annular flap and the valve body which can provide access for fluid to flow into a space between the annular flap and the valve body. In some embodiments, the fluid flow into the space can cause the annular flap to move from a first configuration wherein the flap is closer to the frame to a second configuration wherein the flap is spaced further away from the frame to increase the surface area of the prosthesis and create a barrier to fluid flow exterior to the frame when deployed within the body cavity.

BRIEF DESCRIPTION OF THE DRAWINGS

FIG. 1A is a proximal oriented, perspective view of an embodiment of a prosthesis illustrating a frame, a plurality of anchors, a band, a flap, and a valve body.

FIG. 11A is a partial cross-sectional view of the prosthesis of FIG. 1 with the annular flap in a first configuration.

FIG. 11B is a partial cross-sectional view of the prosthesis of FIG. 11A with the annular flap in a first configuration.

DETAILED DESCRIPTION OF THE PREFERRED EMBODIMENTS

Figure 1B:
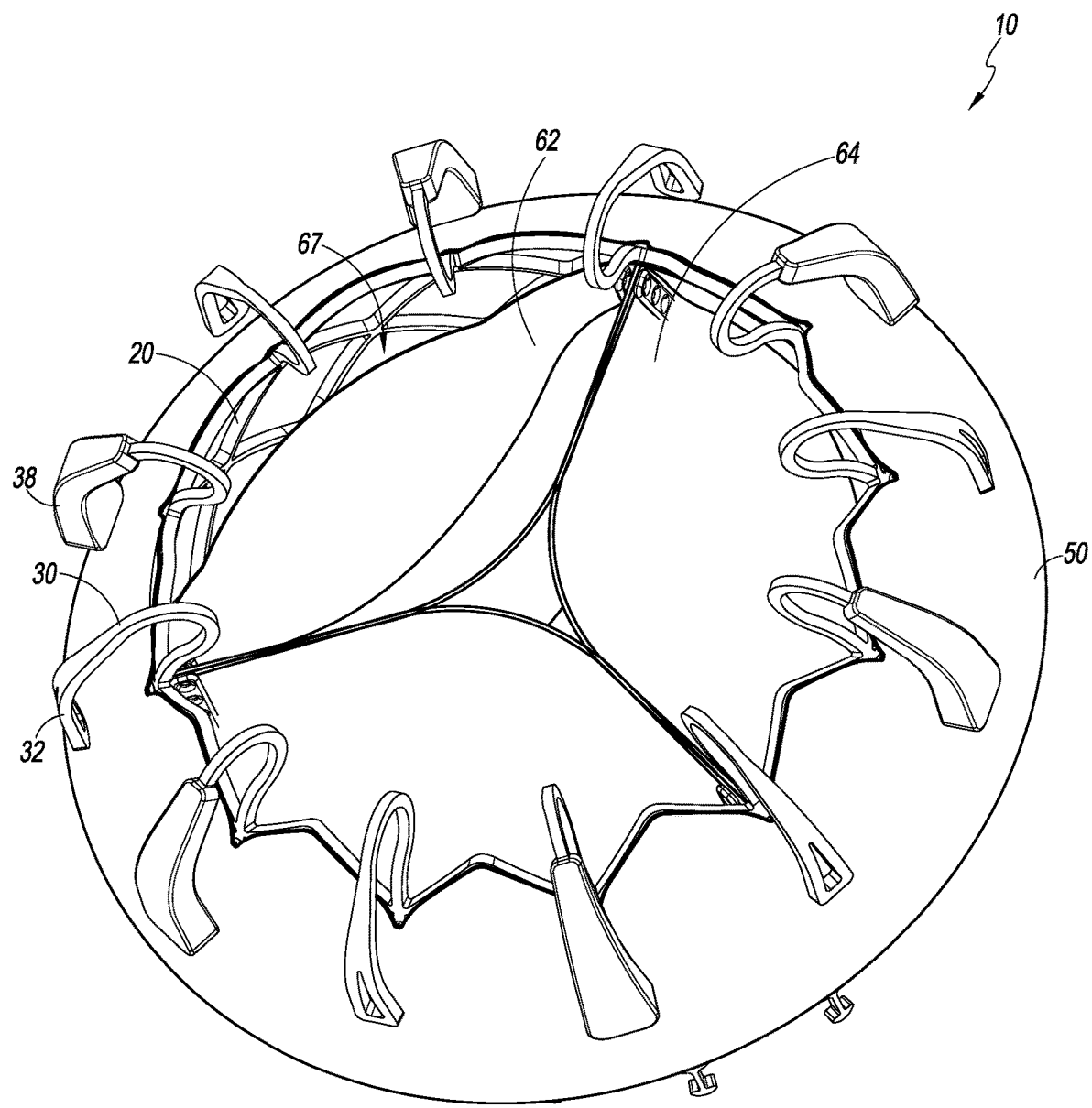
FIG. 1B is a distal oriented, perspective view of the prosthesis of FIG. 1A.

The embodiment of FIGS. 1A-4 illustrates a prosthesis 10. The prosthesis 10 can have components, features, and/or functionality similar to those described in any of U.S. Publication Nos. 2014/0277390, 2014/0277422, and 2014/0277427, the entire contents of all which are incorporated by reference herein. With reference first to the embodiments of FIGS. 1A-4, the prosthesis 10 can include a frame 20, anchors 30, 34, a band 40, an annular flap or sail 50 and a valve body 60. The prosthesis 10 can include a proximal end 12 and a distal end 14 with openings defined at both ends 12, 14 such that fluid can flow therethrough. In some embodiments, the proximal end 12 can be placed in the left atrium while the distal end 14 can be placed in the left ventricle such that prosthesis 10 can function as a replacement for a mitral valve. As will be discussed in greater detail below and as discussed in U.S. Publication Nos. 2014/0277390, 2014/0277422, and 2014/0277427, the prosthesis 10 can allow blood flow in a first direction from the proximal end 12 to the distal end 14 while preventing blood flow in a second direction from the distal end 14 to the proximal end 12. For example, during diastole the valve body 60 may be open to allow blood flow from the proximal end 12 to the distal end 14, and during systole the valve body 60 may be closed to prevent blood flow from the distal end 14 to the proximal end 12.

Figure 2:
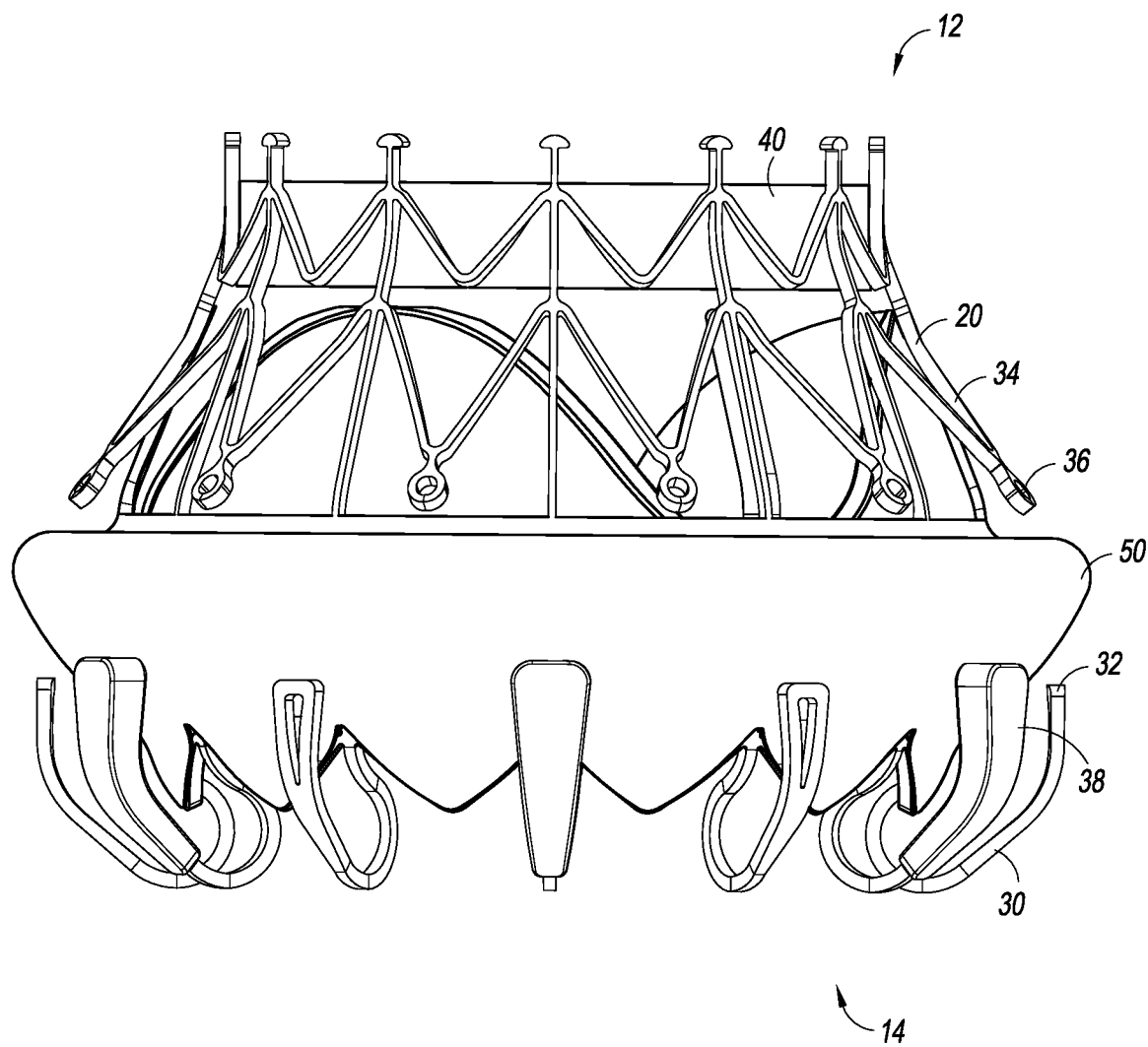
FIG. 2 is a front elevation view of the prosthesis of FIG. 1.
Figure 3:
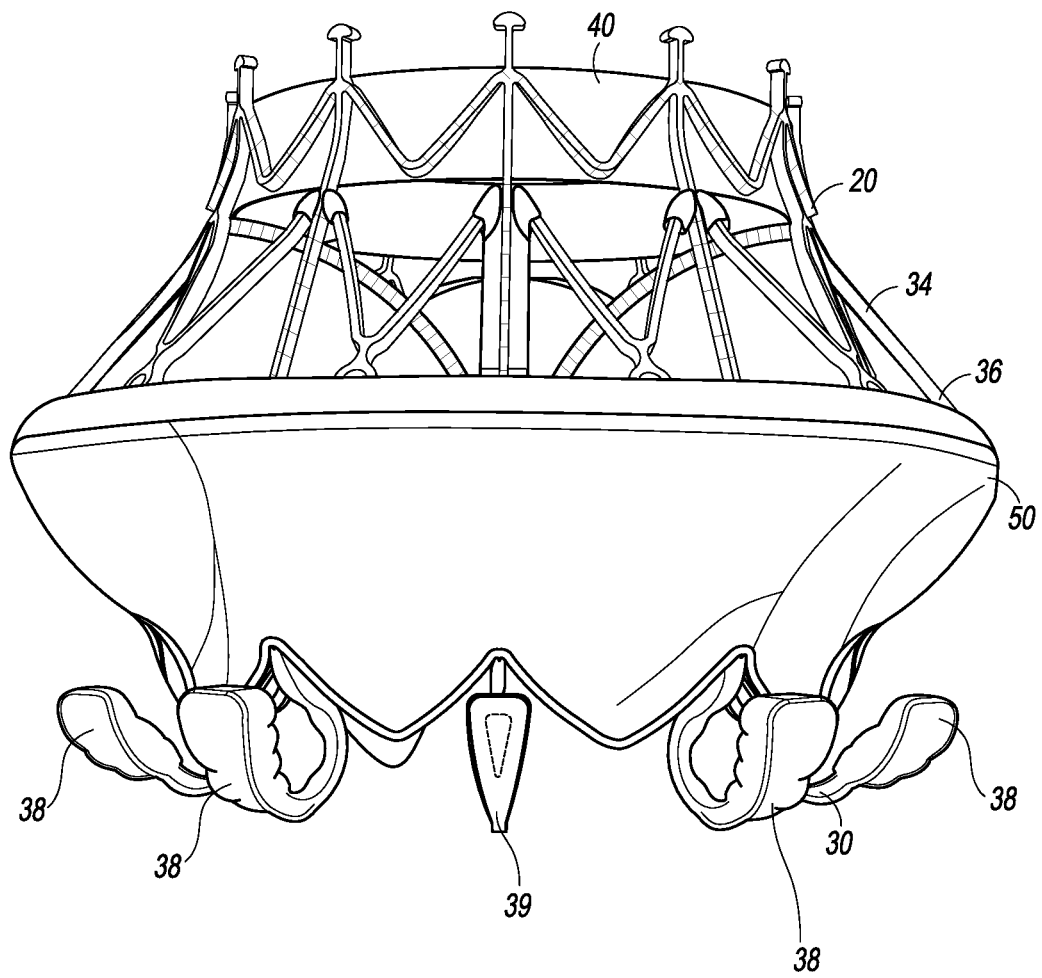
FIG. 3 is a front elevation view of another embodiment of a prosthesis.
Figure 4:
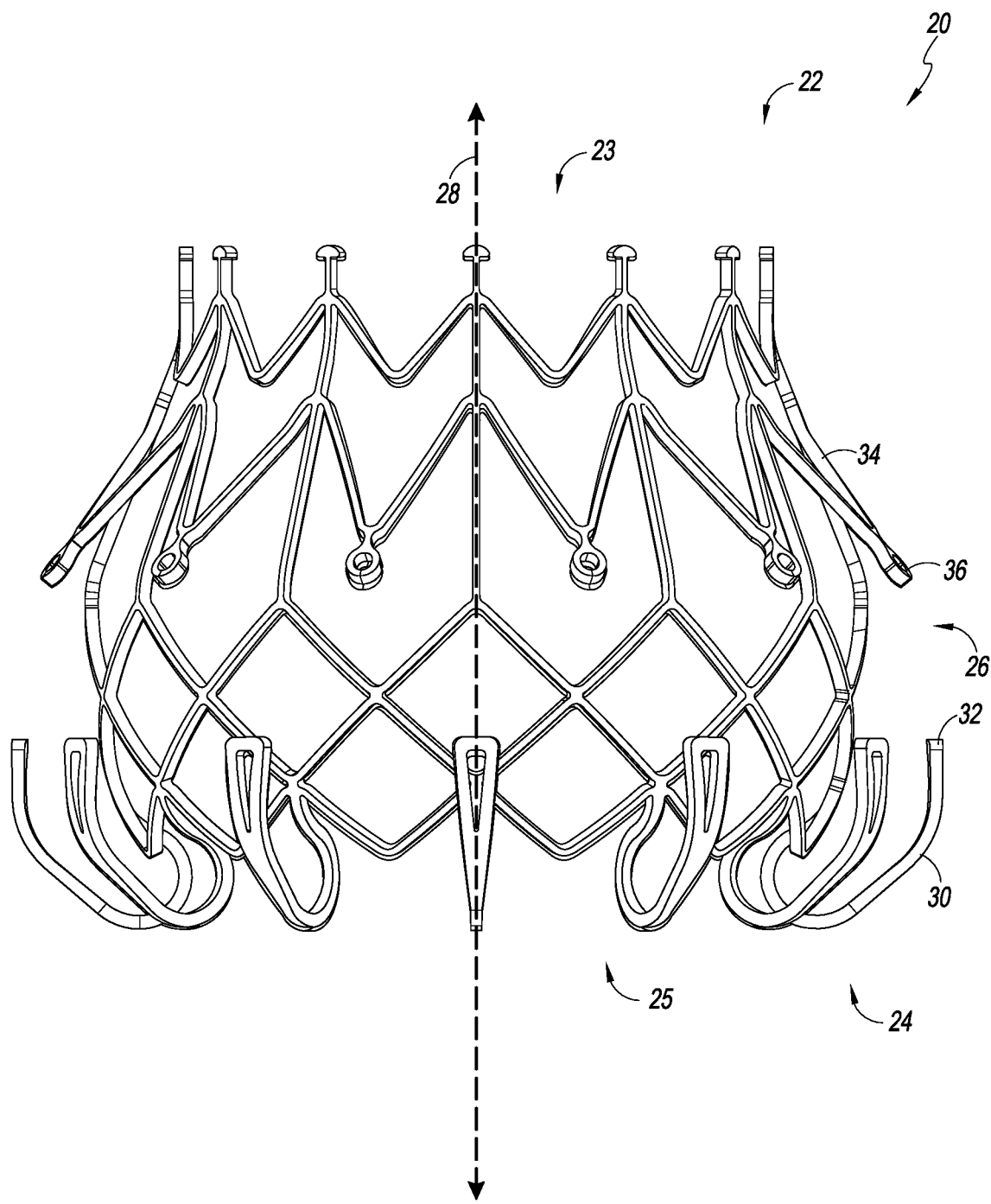
FIG. 4 is a front elevation view of an embodiment of a frame.
Figure 5:
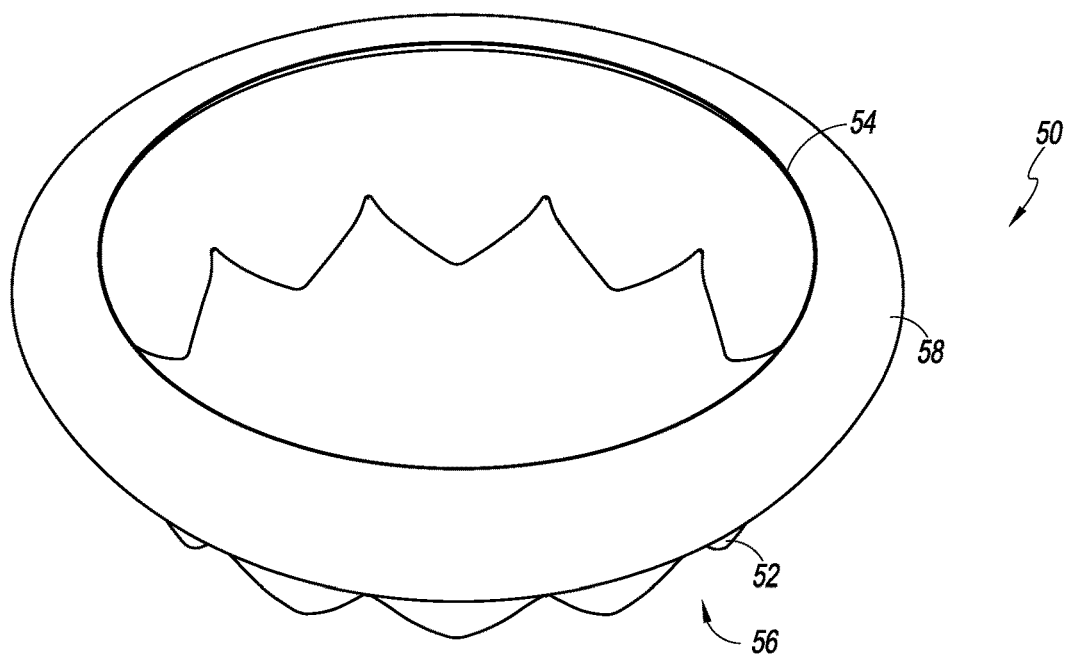
FIG. 5 is a perspective view of an embodiment of an annular flap.

With reference now to the embodiment of FIG. 4, the embodiment illustrates an expandable frame 20 of the prosthesis 10 which can have a proximal end 22 and a distal end 24. In some embodiments, such as the illustrated embodiment, the frame 20 can include an intermediate portion 26 which has a greater diameter than the diameter of the frame 20 at the proximal and/or distal ends 22, 24 when the frame 20 is in an expanded configuration. In some embodiments, such as the illustrated embodiment, the frame 20 can include an intermediate portion 26 which has a greater cross-sectional area than the cross-sectional area of the frame 20 at the proximal and/or distal ends 22, 24 when the frame 20 is in an expanded configuration. The frame 20 can be designed to expand radially and contract for deployment within a body cavity, such as at a heart valve location such as the mitral valve. For example, as described in greater detail in U.S. Publication Nos. 2014/0277390, 2014/0277422, and 2014/0277427, the frame 20 can include a plurality of struts which define a plurality of foreshortening cells. In some embodiments, the frame 20 can be designed to radially and contract radially from a longitudinal axis 28 extending through the frame 20. As illustrated in the embodiments of FIGS. 1-4, the proximal end 22 can define a proximal opening 23 and the distal end 24 can define a distal opening 25.

With continued reference to the embodiments of FIGS. 1A-4 which illustrates the prosthesis 10, in some embodiments the prosthesis 10 can include one or more distal anchors 30. The distal anchors 30 can be positioned along or proximate a distal end 24 of the frame 20 and can be connected to the frame 20. The distal anchors 30 can be designed such that when the frame 20 is in an expanded configuration an end or tip 32 of each distal anchor 30 is positioned radially outward from the frame 20 and extends generally in a proximal direction. In some embodiments, the prosthesis 10 can include one or more proximal anchors 34. The proximal anchors 34 can be positioned along or proximate a proximal end 22 of the frame 20 and can be connected to the frame 20. The proximal anchors 34 can be designed such that when the frame 20 is in an expanded configuration an end or tip 36 of each proximal anchor 34 is positioned radially outward from the frame 20 and extends generally in a distal direction. In some embodiments, one or more anchors 30, 34 can include cushions 38, 39 covering one or more of such anchors.

In some embodiments, the cushion 38 can be formed from two separate pieces of material such as an inner portion positioned within a covering such that the covering forms a layer surrounding the inner portion. For example, the inner portion can be wholly contained within the covering. In some embodiments, the inner portion can be formed of a foam material such that the inner portion is at least somewhat compliant and the covering can be formed of a biocompatible, fabric material. The embodiment of FIGS. 1A, 1B and 2 illustrates cushions 38 on alternating distal anchors 30, the cushions 38 extending partially from an end or tip of the anchor 30 towards the connection between the anchor 30 and the frame 20. Use of cushions 38 on alternating distal anchors 30 can maintain a smaller form factor while in the prosthesis 10 is in a contracted state for delivery. As such, for embodiments having twelve distal anchors 30, a total of six distal anchors 30 can have cushions 38 and a total of six distal anchors 30 may not have a cushion 38. The cushions 38 can advantageously increase contact area of the anchors 30 on tissue. This can reduce trauma between the anchor 30 and such tissue. Moreover, this can facilitate growth of tissue in and/or around the anchor 30 in embodiments where the cushions 38 are formed of a material which encourages tissue growth. The cushions 38 on anchors 30 adjacent anchors 30 without a cushion 38 can also beneficially reduce any potential trauma caused by adjacent anchors 30 without a cushion 38.

The embodiment of FIG. 3 illustrates cushions 38, 39 on all distal anchors 30. As shown some of the distal anchors 30 include thicker cushions 38 than other distal anchors 30. The cushions 38, 39 can extend the majority or entirety of the length of the anchor 30 from an end or tip of the anchor 30 towards the connection between the anchor 30 and the frame 20. As shown, two distal anchors 30 include thicker cushions 38 with a distal anchor 30 having a thinner cushion 39 positioned therebetween. As such, for embodiments having twelve distal anchors 30, a total of eight distal anchors 30 can have thicker cushions 38 and a total of four distal anchors 30 can include thinner cushions 39. The thicker cushions 38 can be formed of an inner portion and a cover layer, with the inner portion being formed from a compliant material, such as foam, and the covering can be formed of a biocompatible, fabric material. As shown, the inner portion can be positioned only around a portion of the anchor 30 whereas the covering can extend the majority or entirety of the length of the anchor 30. The thinner cushion 39 can be a cover layer with a thinner inner portion or without an inner portion. The inner portion and/or the covering can be formed of a material which encourages tissue growth.

Other configurations of cushions 38, 39 can also be used. For example, in some embodiments, the cushions 38, 39 can be included on proximal anchors 34. In some embodiments, the cushions 38, 39 can be positioned on other portions of the frame 20 such as, but not limited to, one or more of the struts forming the frame 20. The cushions 38, 39 can advantageously increase contact area of the prosthesis 10 on tissue. This can reduce trauma between the frame 20 and such tissue. Moreover, this can facilitate growth of tissue in and/or around the frame 20 in embodiments where the cushions 38, 39 are formed of a material which encourages tissue growth. In some embodiments, the covering of cushions 38, 39 can extend from the annular flap 50 and be formed from materials similar to those of the annular flap 50. The covering of cushions 38, 39 can cover a majority or the entirety of the distal anchors 30 as shown in FIG. 3. In some embodiments, the cushions 38, 39 can be attached to the distal anchors 30 via circumferential stitching about a longitudinal axis of the distal anchor 30.

With reference to the embodiments of FIGS. 1A-3, in some embodiments the prosthesis 10 can include a band 40 along or proximate the proximal end 22 of the frame 20. The band 40 can include features and perform functions similar to those described in U.S. patent application Ser. No. 13/403,929 filed Feb. 23, 2012, titled REPLACEMENT VALVE AND METHOD, published as U.S. Publication No. 2012/0215303, the entire contents of which is incorporated by reference herein.

With reference to the embodiments of FIGS. 1A-3, 5 and 6, the prosthesis 10 can include an annular flap 50 which can be positioned around and secured to an exterior of the frame 20. The annular flap 50 can have a distal edge 52 secured at or proximate the distal end 24 of the frame 20 and extend to a proximal edge 54 secured at or proximate an intermediate location, such as the intermediate portion 26, on the frame 20 between the proximal and distal ends 22, 24. In some embodiments, the distal edge 52 of the annular flap 50 can be provided with a shape that generally corresponds to the shape of the frame 20. This can facilitate the securement of the flap 50 to the frame 20. For example, as illustrated in the embodiments of FIGS. 1A-3, 5 and 6, the distal edge 52 can include a generally triangular pattern 56 which follows the generally triangular, zig-zag or undulating pattern of the struts of frame 20 along the distal end 24 of frame 20. Other shapes and/or patterns 56 can be used along the distal edge 52 of the annular flap 50. In some embodiments, the distal edge 52 of the annular flap 50 can have no pattern. In some embodiments the distal edge 52 does not follow the pattern of the struts of the frame 20 and/or can have a different pattern from that of the struts.

In some embodiments, such as the embodiments of FIGS. 1A-3, 5 and 6, the annular flap 50 can have a flange 58. The flange 58 can extend generally radially outward in a direction generally orthogonal to the longitudinal axis 28 extending through the frame 20. In some embodiments, the flange 58 can also project proximally and/or distally. The flange 58 can be used to further prevent or inhibit backflow of fluids around the prosthesis 10. In some embodiments, the flange 58 can be formed from a first layer of resilient material, such as polyethylene terephthalate (PET) or any other biocompatible material, which extends radially outward from the frame 10. In some embodiments, a second layer of resilient material, such as PET or any other biocompatible material, can extend from the first layer in a distal direction towards a distal end 24 of the frame 20. In some embodiments, the first and second layers can be connected together using a suitable mechanism such as adhesives or sutures. In some embodiments, the annular flap 50 can be formed from a single layer of resilient material. In some embodiments, the first and/or second layers can be formed from a deformable material. In some embodiments, the first and/or second layers can be formed from a material which is wholly or substantially fluid impermeable. The annular flap 50 can also include other structures, such as wires formed from resilient materials such as nitinol, to allow at least portions of the annular flap 50 to retain a particular shape. These structures may be positioned on an inner surface of the annular flap 50.

Figure 6:
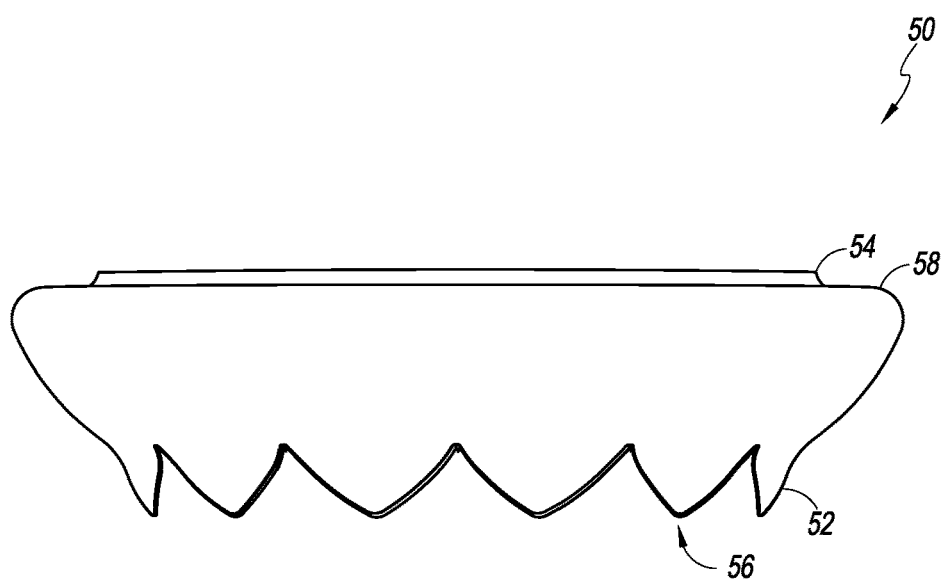
FIG. 6 is a front elevation view of the annular flap of FIG. 5.
Figure 7:
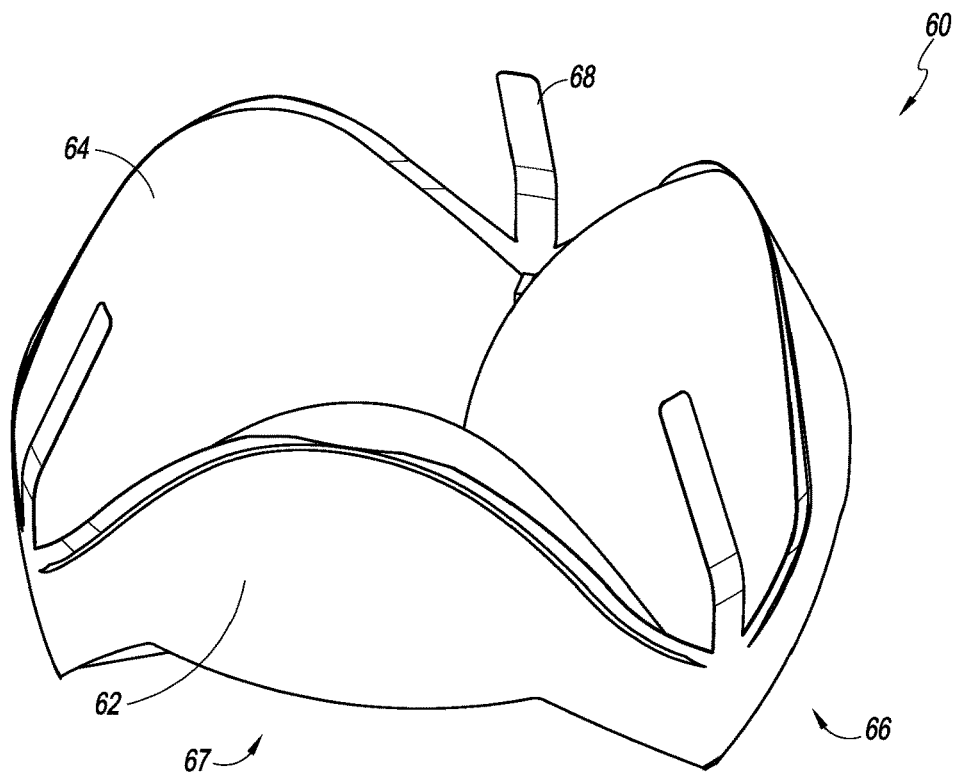
FIG. 7 is a perspective view of an embodiment of a valve body.
Figure 8:
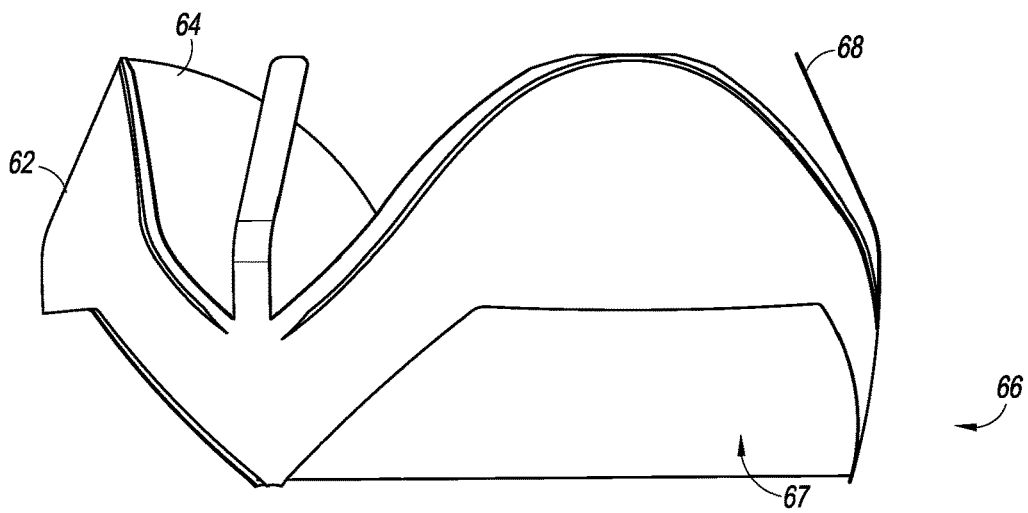
FIG. 8 is a front perspective view of the valve body of FIG. 7.

In some embodiments, the flange 58 can be formed when the annular flap 50 is in an expanded configuration. When the flap is in an expanded configuration, such as illustrated in the embodiment of FIG. 6, the radius of the annular flap 50 can decrease distal of the flange 58. As will be described in further detail below, the annular flap 50 can have a first, collapsed or deflated configuration in which the flap 50 is closer to the frame 20 to a second, expanded or inflated configuration in which the flap 50 is spaced further away from the frame 20. The expanded configuration can increase the surface area of the prosthesis 10 and create a barrier to fluid flow exterior to the frame 20 when deployed within a body cavity. The transition from the first configuration to the second configuration, and from the second configuration to the first configuration, can be triggered by blood flow into and out of the interior region of the flap 50, as described further below.

Figure 9:
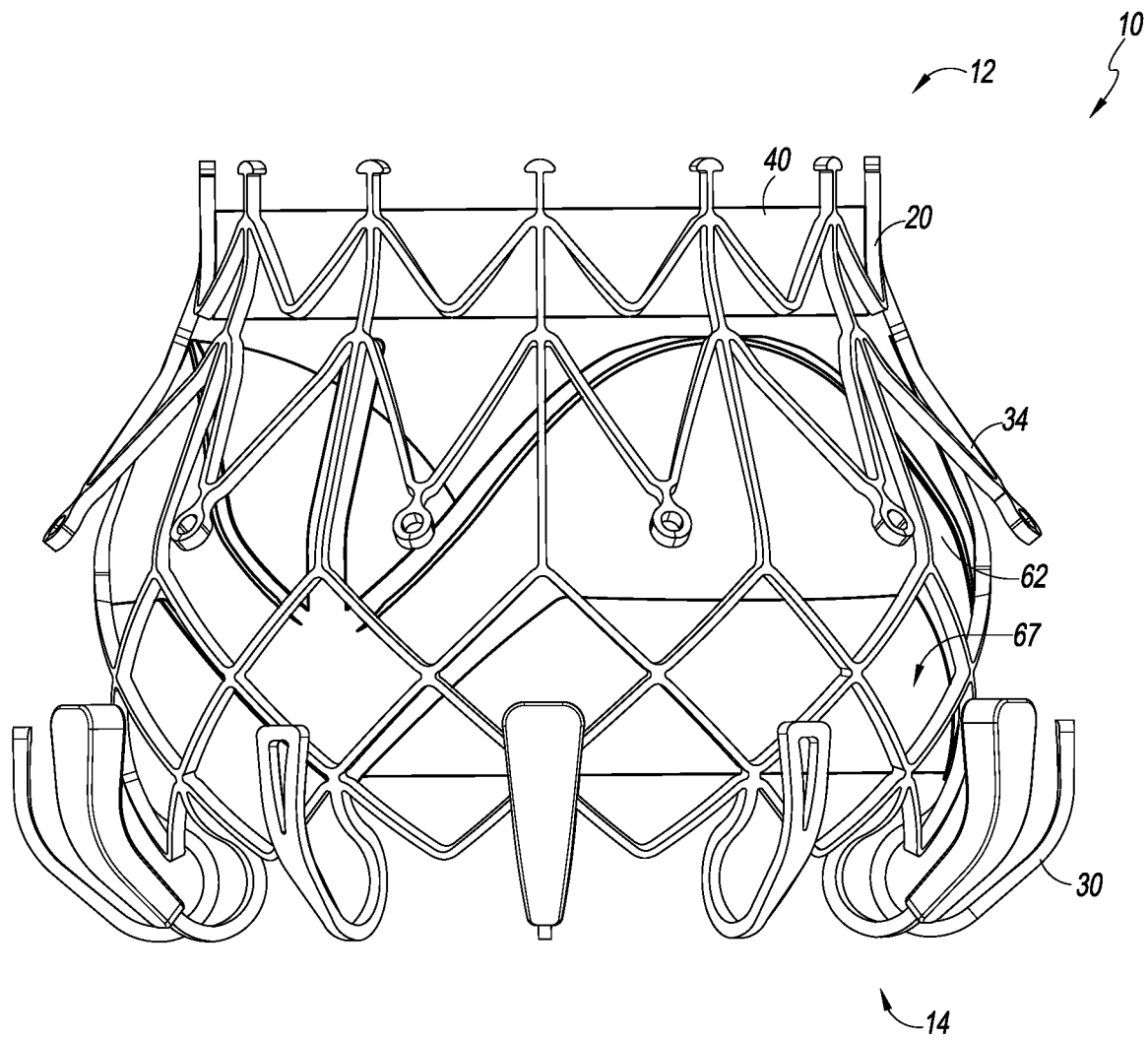
FIG. 9 is a front elevation of an embodiment of a prosthesis illustrating a frame, a plurality of anchors, a band, a flap, and a valve body.
Figure 10:
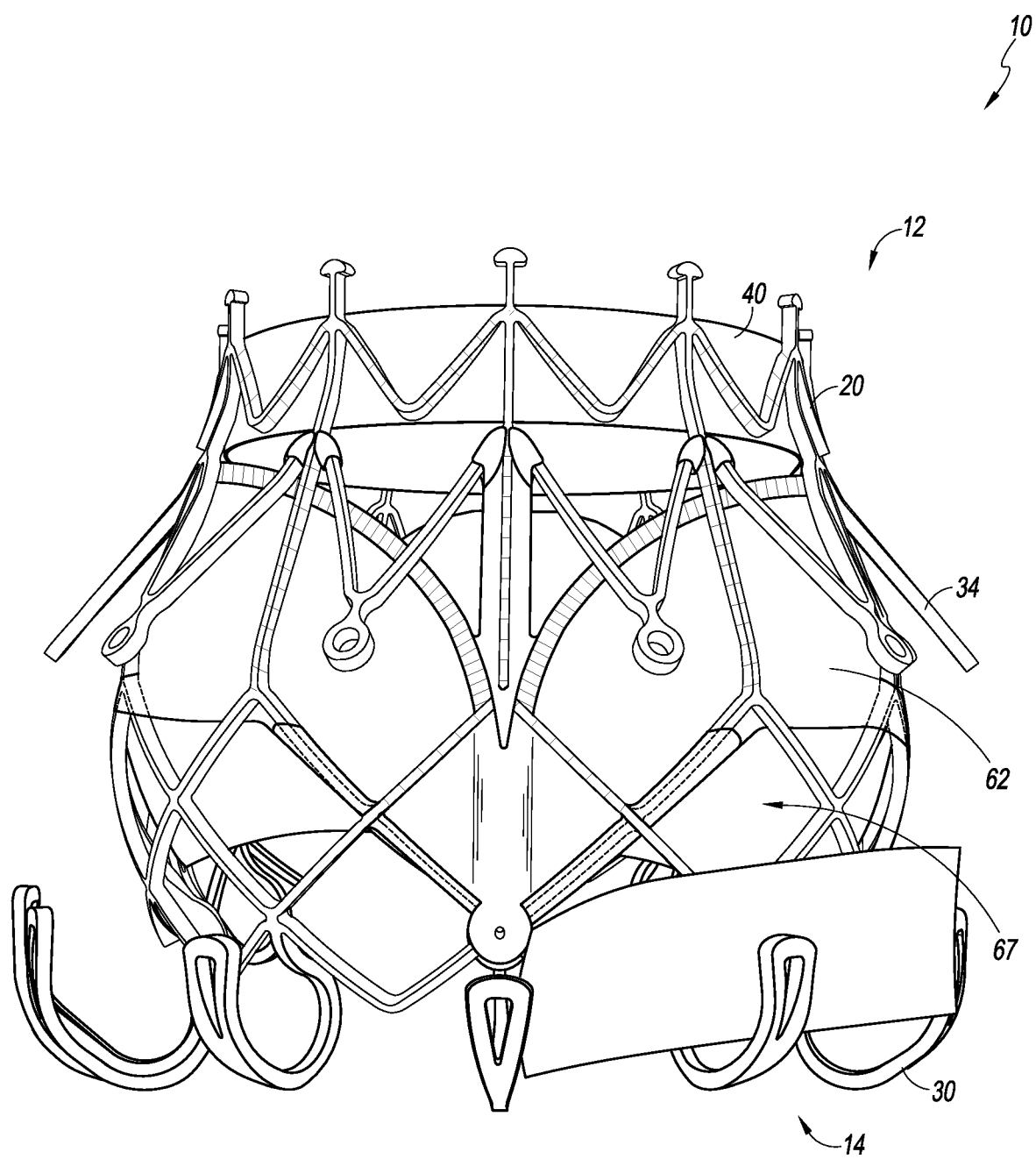
FIG. 10 is a front elevation another embodiment of a prosthesis.

With reference to the embodiments of FIGS. 1A-3 and 7-10, the prosthesis 10 can include a valve body 60 positioned within an interior of the frame 20. In some embodiments, the valve body 60 can include an inner skirt 62 secured to the interior of the frame 20. The valve body 60 can include a plurality of leaflets 64 which can be designed to allow flow in a first direction, such as a proximal to distal direction, while preventing flow in a second direction, such as a distal to proximal direction. In some embodiments, the leaflets 64 have a curved, proximal edge which is fixed to the inner skirt 62 and a distal edge which freely moves. In such embodiments, movement of the distal edges towards and away from each other can allow the valve body 60 to open and close depending on the direction of flow. Accordingly, the valve body 60 can function as a one-way valve such as a mitral valve. In some embodiments, the leaflets 64 are secured to the inner skirt 62. The leaflets 64 and the inner skirt 62 can be manufactured from the same material or from different materials. For example, the inner skirt 62 can be manufactured from a more rigid material than the leaflets 64. In some embodiments, the distal end 66 of the inner skirt 62 can be secured at or proximate the distal end 24 of the frame 20. In some embodiments, such as is illustrated in the embodiments of FIGS. 9 and 10, the distal end 66 of the inner skirt 62 can be positioned slightly proximal of the distal end 24 of the frame 20. This can allow facilitate blood flow around the outside of the inner skirt 62 and into the annular flap 50. The inner skirt 62 can include one or more openings or cutouts 67 positioned along a distal end 66 of the inner skirt 62. This can further facilitate blood flow around the outside of the inner skirt 62. In some embodiments, the valve body 60 can include arms 68 to further secure the valve body 60 to the frame 20.

Figure 12A:
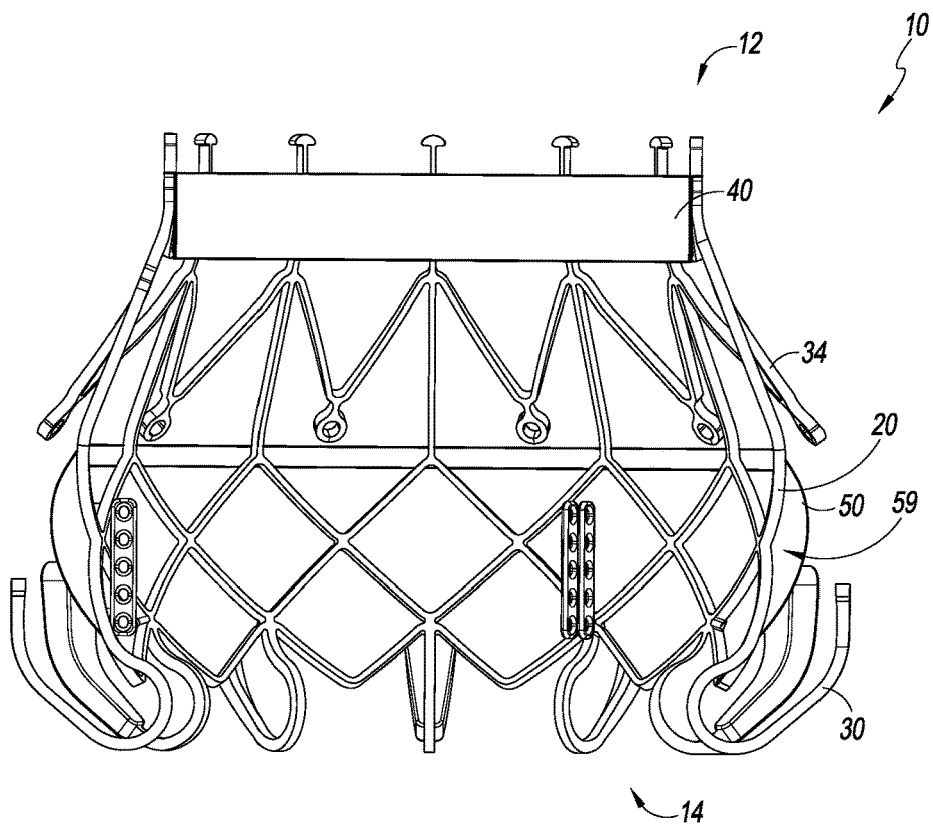
FIG. 12A is a partial cross-sectional view of the prosthesis of FIG. 1 with the annular flap in a first configuration, the valve body being removed.
Figure 12B:
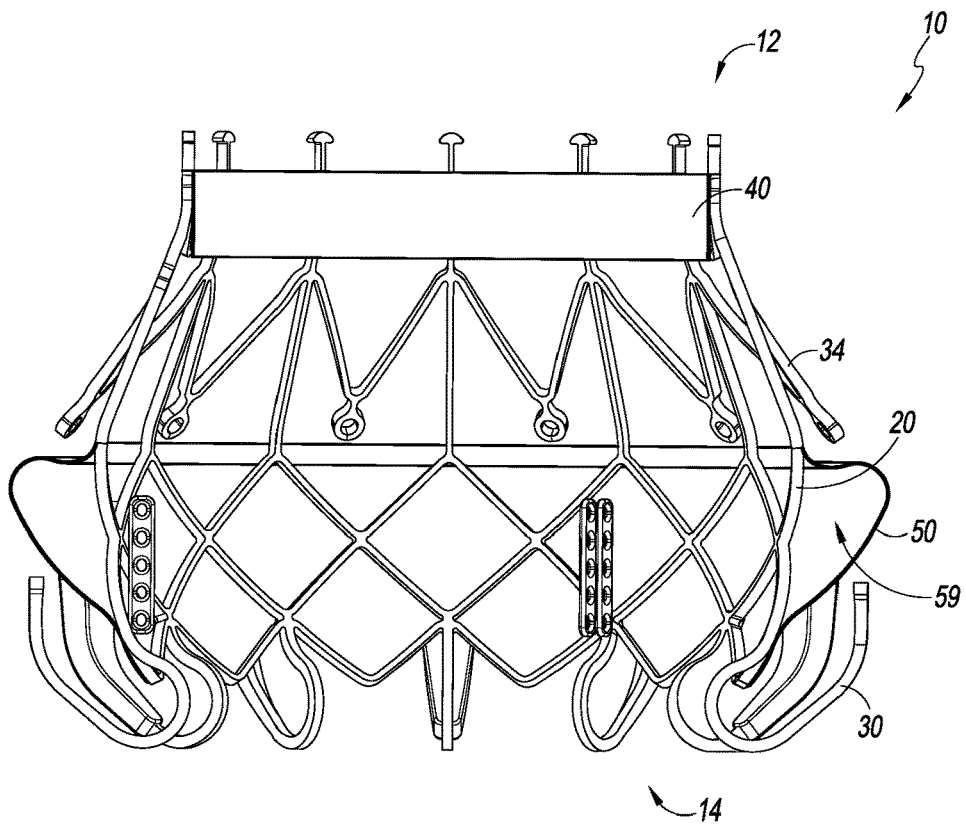
FIG. 12B is a partial cross-sectional view of the prosthesis of FIG. 12A with the annular flap in a first configuration.

Reference is now made to the embodiments of FIGS. 11A-B and 12A-B which illustrate two configurations of the annular flap. It should be noted that the embodiment of FIGS. 12A-B is similar to the embodiment of FIG. 11A-B with the valve body 60 removed. As shown in the embodiments of FIGS. 11A and 12A, in a first configuration the annular flap 50 is positioned closer to the frame 20. In the event that fluid flows in a second direction, such as a distal to proximal direction, at least a portion of the fluid can enter into an opening between the frame 20 and the annular flap 50, such as opening or cutout 67 formed along the distal end 66 of the inner skirt 62, and collect within a space 59 such that the annular flap 50 takes on the second configuration as shown in the embodiments of FIGS. 11B and 12B. As shown in the embodiments of FIG. 1B, the frame 20 can be positioned within the space 59 between the annular flap 50 and the valve body 60. This effect can be enhanced if the valve body 60 is designed to prevent fluid flow in the second direction (e.g., distal to proximal), such that a substantial portion of fluid is forced around and into the annular flap 50. The annular flap 50 can revert back to the first configuration when fluid flows in a first direction, such as a proximal to distal direction, such that fluid is expelled from within the space 59. In some embodiments, the space 59 can be formed between the inner skirt 62 and the flap 50. For example, both the inner skirt 62 and the flap 50 can be connected to the frame 20 along this region, such as along a proximal edge 54 of the flap 50, such that the inner skirt 62 and flap 50 serve as a barrier to flow of fluid outward from space 59.

Reference is now made to FIG. 13A-15 which illustrate schematic representations of an embodiment of a replacement heart valve 10 positioned within a native mitral valve of a heart 100. A portion of the native mitral valve is shown schematically and represents typical anatomy, including a left atrium 102 positioned above an annulus 106 and a left ventricle 104 positioned below the annulus 106. The left atrium 102 and left ventricle 104 communicate with one another through a mitral annulus 106. Also shown schematically in FIGS. 13A-15 is a native mitral leaflet 108 having chordae tendineae 110 that connect a downstream end of the mitral leaflet 108 to the papillary muscle of the left ventricle 104. The portion of the replacement heart valve 10 disposed upstream of the annulus 106 (toward the left atrium) can be referred to as being positioned supra-annularly. The portion generally within the annulus 106 is referred to as positioned intra-annularly. The portion downstream of the annulus 106 is referred to as being positioned sub-annularly (toward the left ventricle). In the illustrated embodiment, only a part of the foreshortening portion is positioned intra-annularly or sub-annularly, and the rest of the replacement heart valve 10 is supra-annular.

Figure 13A:
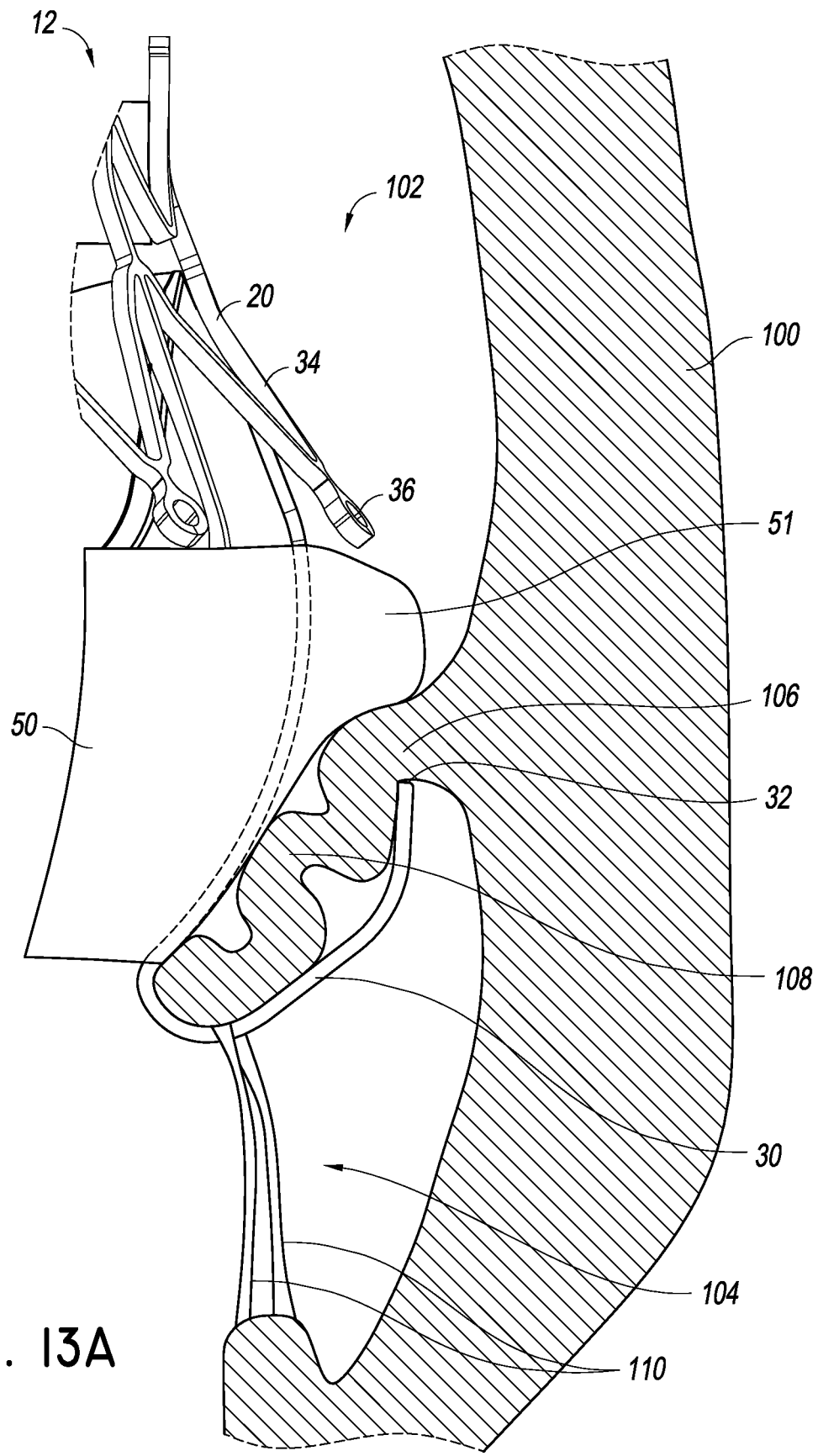
FIG. 13A-15 illustrate schematic representations of the prosthesis of FIG. 3 positioned within a heart, with FIGS. 13A-13C illustrating the prosthesis in situ with distal anchors contacting the ventricular side of a mitral valve annulus, FIGS. 14A-14B illustrating the prosthesis in situ with distal anchors not contacting the ventricular side of the mitral valve annulus, and FIG. 15 illustrating the prosthesis in situ with distal anchors not extending between the chordae tendineae.
Figure 13B:
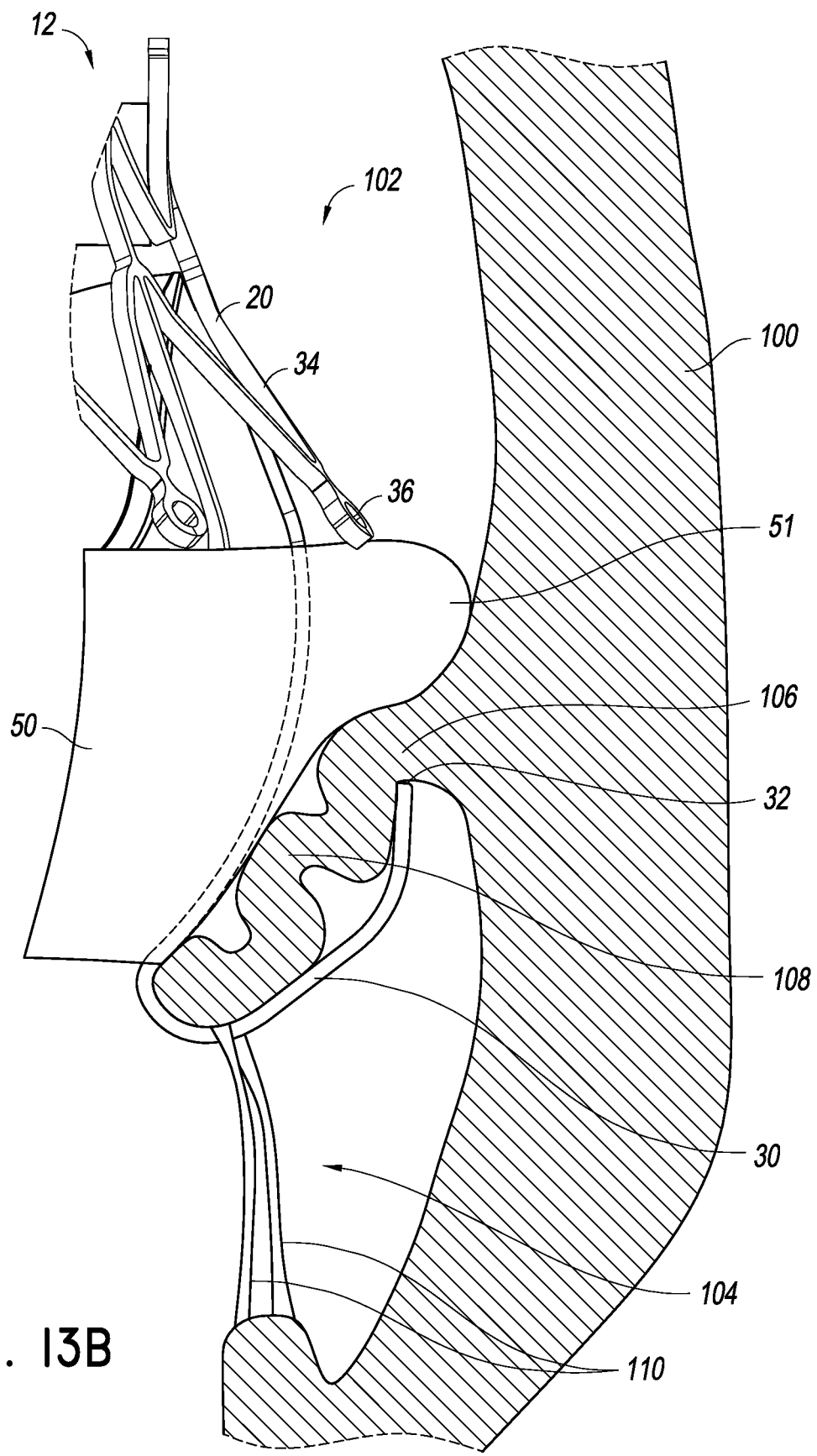
Figure 13C:
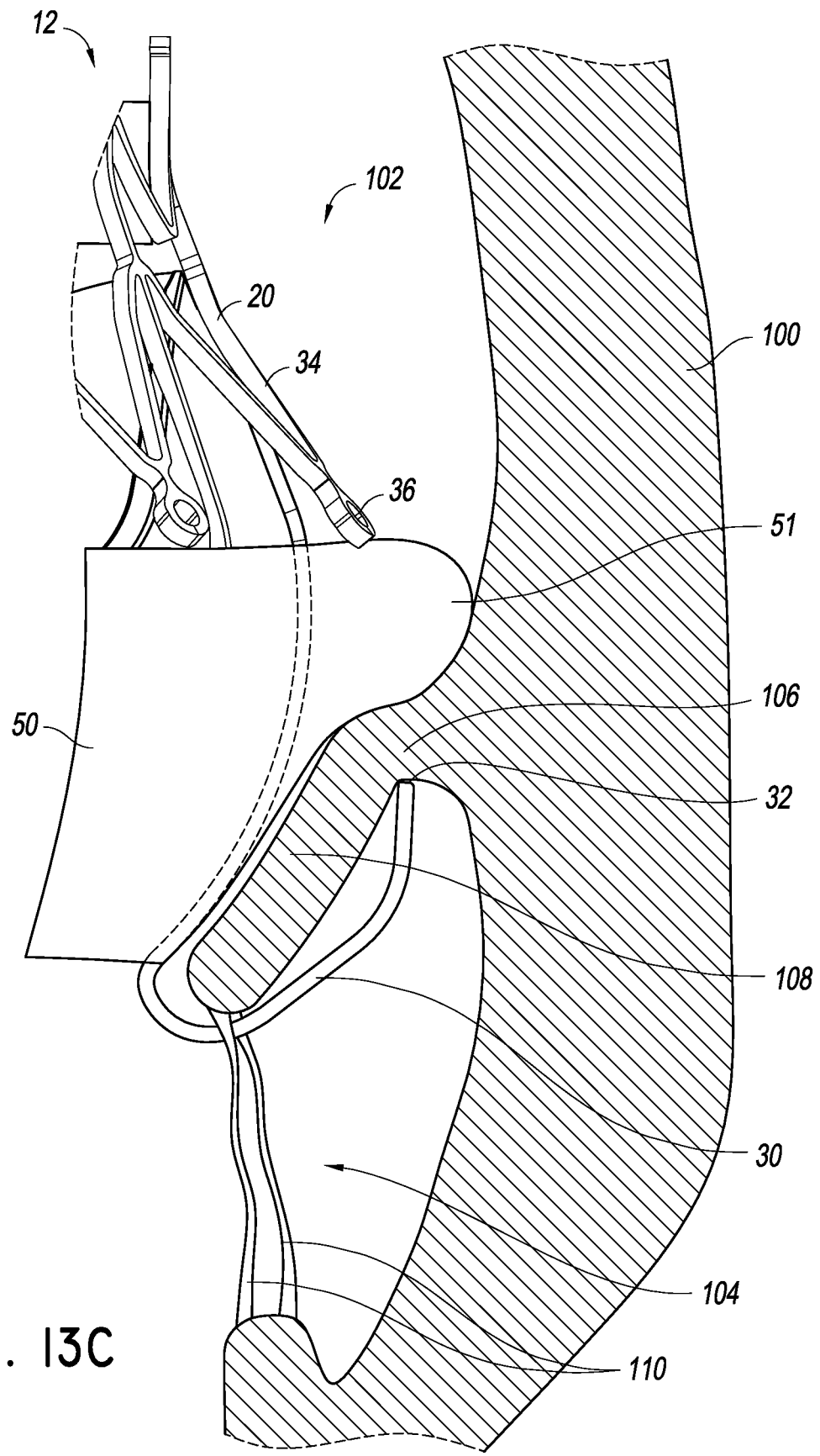
Figure 14A:
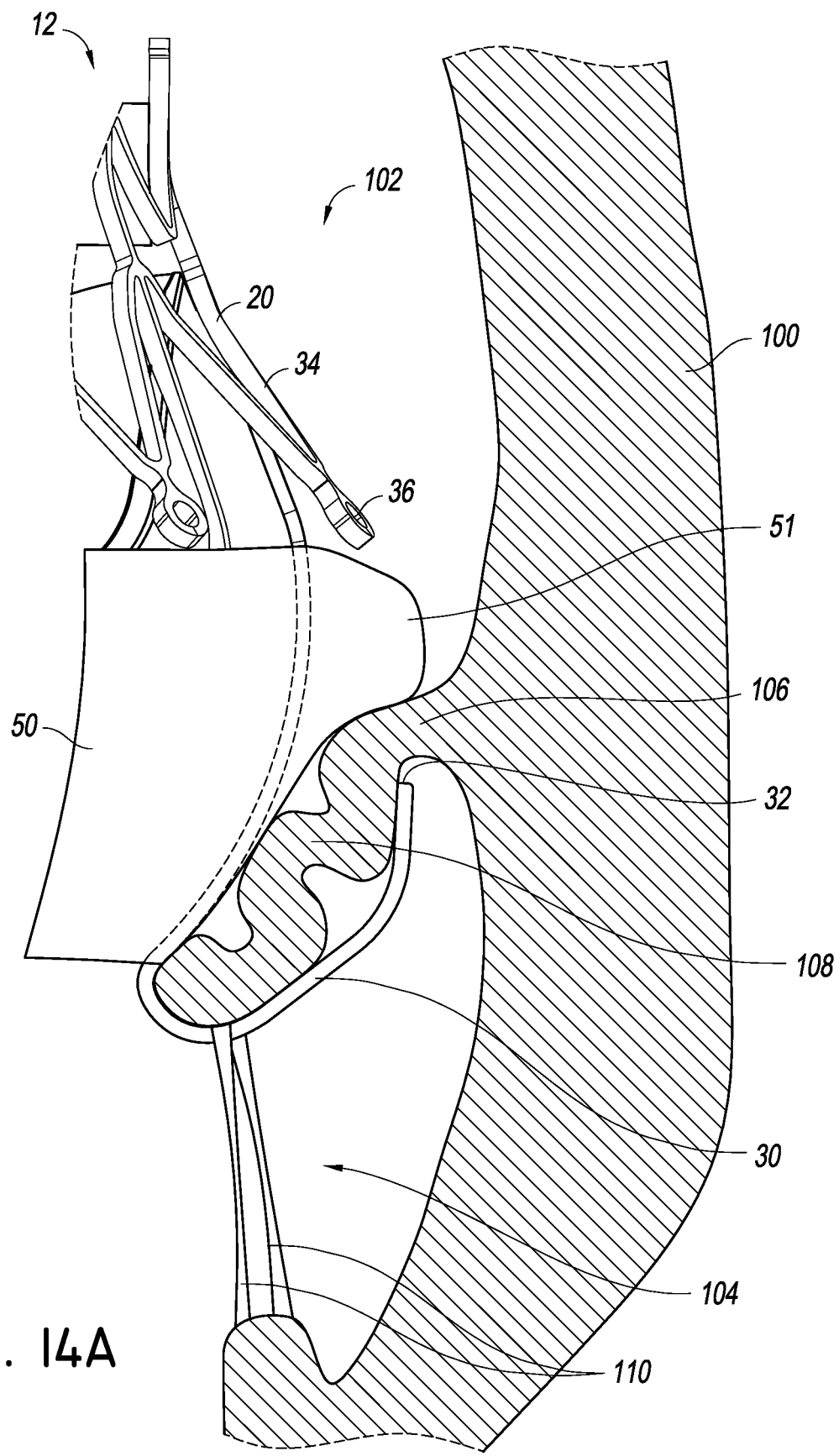
Figure 14B:
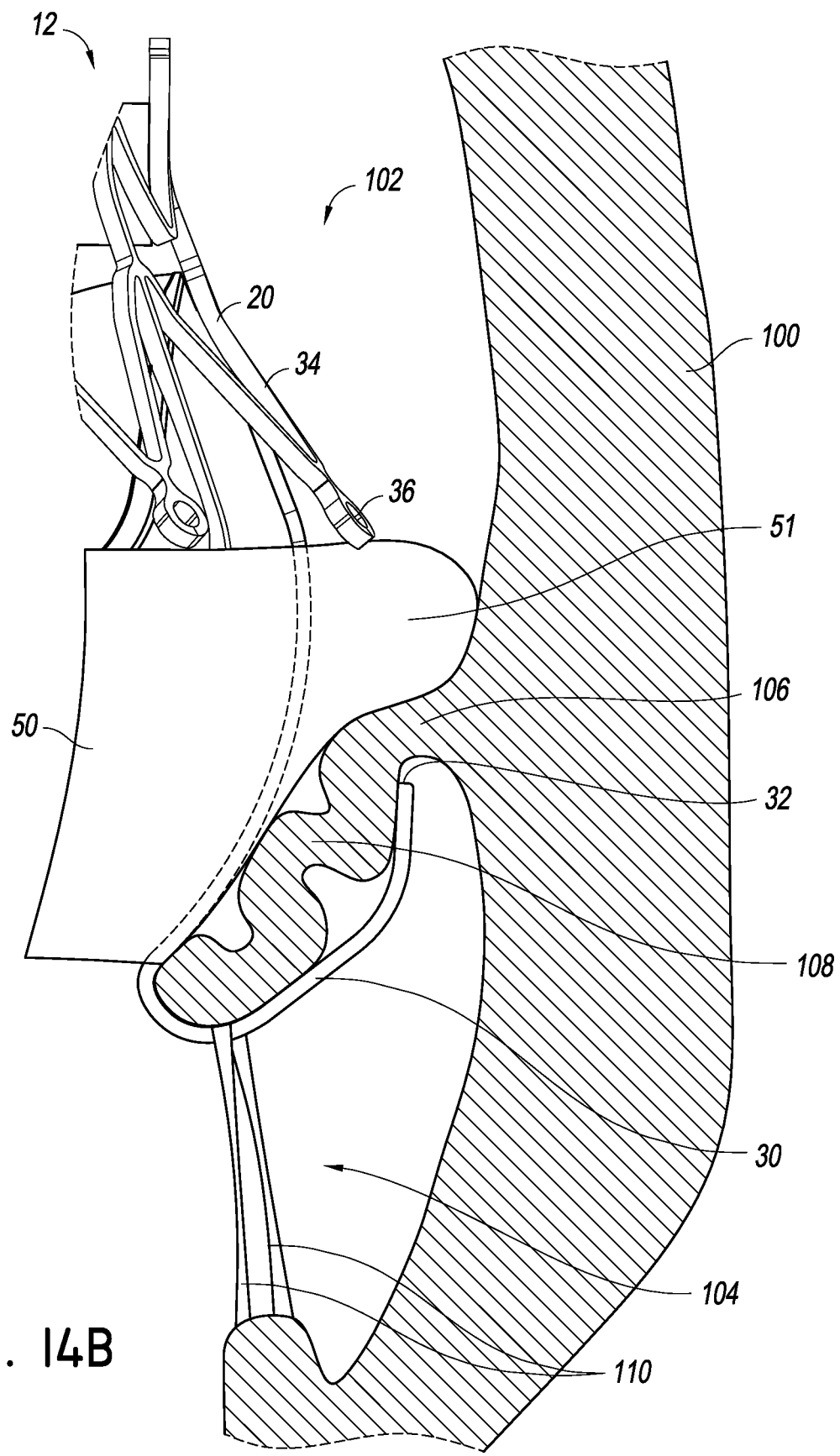
Figure 15:
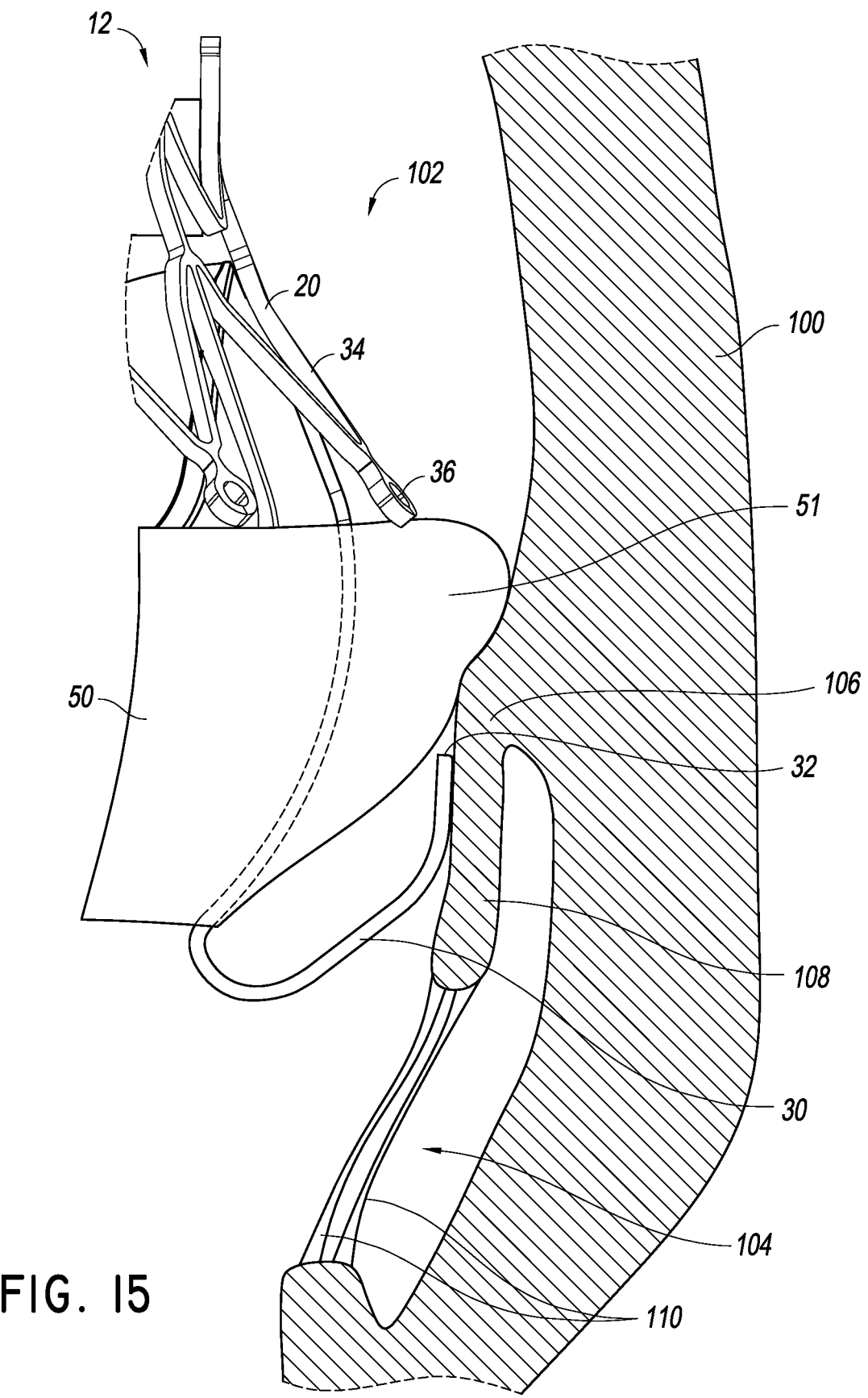

As shown in the situations illustrated in FIGS. 13A-14, the replacement heart valve 10 can be disposed so that the mitral annulus 106 is between the distal anchors 30 and the proximal anchors 34. In some situations, the prosthesis 10 can be positioned such that ends or tips 32 of the distal anchors 30 contact the annulus 106 as shown, for example, in FIGS. 13A-13C. In some situations, the prosthesis 10 can be positioned such that ends or tips 32 of the distal anchors 30 do not contact the annulus 106 as shown, for example, in FIGS. 14A-14B. In some situations, the prosthesis 10 can be positioned such that the distal anchors 30 do not extend around the leaflet 108 as shown in FIG. 15. While FIGS. 13A-15 are described separately below, it should be understood that one or more of the situations illustrated in FIGS. 13A-15 may be present when the prosthesis 10 is positioned at the implantation location, such as a native mitral valve. For example, in some situations the prosthesis 10 may be positioned such that some distal anchors 30 may contact the annulus 106 while other distal anchors 30 may not.

With reference first to the situations illustrated in FIGS. 13A-14B, the replacement heart valve 10 can be positioned so that the ends or tips 32 of the distal anchors 30 are on a ventricular side of the mitral annulus 106 and the ends or tips of 36 the proximal anchors 34 are on an atrial side of the mitral annulus 106. The distal anchors 30 can be positioned such that the ends or tips 32 of the distal anchors 30 are on a ventricular side of the native leaflets beyond a location where chordae tendineae 110 connect to free ends of the native leaflets. The distal anchors 30 may extend between at least some of the chordae tendineae 110 and, in some situations such as those shown in FIGS. 13A-13C, can contact or engage a ventricular side of the annulus 106. It is also contemplated that in some situations, such as those shown in FIGS. 14A and 14B, the distal anchors 30 may not contact the annulus 106, though the distal anchors 30 may still contact the native leaflet 108. In some situations, the distal anchors 30 can contact tissue of the left ventricle 104 beyond the annulus 106 and/or a ventricular side of the leaflets.

During delivery, the distal anchors 30 (along with the frame 20) can be moved toward the ventricular side of the annulus 106 with the distal anchors 30 extending between at least some of the chordae tendineae 110 to provide tension on the chordae tendineae 110. The degree of tension provided on the chordae tendineae 110 can differ. For example, little to no tension may be present in the chordae tendineae 110 as shown in FIG. 13C where the leaflet 108 is shorter than or similar in size to the distal anchors 30. A greater degree of tension may be present in the chordae tendineae 110 as shown in FIGS. 13A and 13B where the leaflet 108 is longer than the distal anchors 30 and, as such, takes on a compacted form and is pulled proximally. An even greater degree of tension may be present in the chordae tendineae 110 as shown in FIGS. 14A and 14B where the leaflets 108 are even longer relative to the distal anchors 30. As shown in FIGS. 14A and 14B, the leaflet 108 is sufficiently long such that the distal anchors 30 do not contact the annulus 106.

The proximal anchors 34 can be positioned such that the ends or tips 36 of the proximal anchors 34 are adjacent the atrial side of the annulus 106 and/or tissue of the left atrium 102 beyond the annulus 106. In some situations, some or all of the proximal anchors 34 may only occasionally contact or engage atrial side of the annulus 106 and/or tissue of the left atrium 102 beyond the annulus 106. For example, as shown in FIGS. 13A and 13B, the proximal anchors 34 may be spaced from the atrial side of the annulus 106 and/or tissue of the left atrium 102 beyond the annulus 106. The proximal anchors 34 could provide axial stability for the prosthesis 10. In some situations such as those shown in FIGS. 13A and 14A, some or all of the proximal anchors 34 may not contact the annular flap 50. This may occur when the annular flap 50 is in a collapsed configuration although it may also occur when the annular flap 50 is in an expanded configuration. In some situations such as those shown in FIGS. 13B, 13C and 14B, some or all of the proximal anchors 34 may contact the annular flap 50. This may occur when the annular flap 50 is in an expanded configuration although it may also occur when the annular flap 50 is in a collapsed configuration. It is also contemplated that some or all of the proximal anchors 34 may contact the atrial side of the annulus 106 and/or tissue of the left atrium 102 beyond the annulus 106

With continued reference to the situations illustrated in FIGS. 13A-14B, the annular flap 50 can be positioned such that a proximal portion 51 of the annular flap 50 is positioned along or adjacent an atrial side of the annulus 106. The proximal portion 51 can be positioned between the atrial side of the annulus 106 and the proximal anchors 34. The proximal portion 51 can extend radially outward such that the annular flap 50 is positioned along or adjacent tissue of the left atrium 102 beyond the annulus 106. The annular flap 50 can create a seal over the atrial side of the annulus 106 when the flap 50 is in the expanded state.

The flap 50 can transition from the collapsed state to the expanded state during systole when pressure in the left ventricle 104 increases. This increased pressure within the left ventricle 104 can cause blood within the left ventricle 104 to be directed to areas of lower pressure, such as the aorta (not shown) and the left atrium 102. As noted above, during systole the valve body 60 may be closed to prevent blood from flowing back into the left atrium 102. A substantial portion of blood can forced around the frame 20 and valve body 60 and into the annular flap 50 such that the flap 50 can expand. Sealing along an atrial side of the annulus 106 can be particularly effective. The left atrium 102 can be at a lower pressure in comparison to the pressure of the space 59 between the annular flap 50 and the valve body 50, which is closer to the pressure of the left ventricle 104. The existence of such a pressure differential between the left atrium 102 and the space 59 during systole can allow the flap 50 to apply a greater force to surrounding tissue within the left atrium 102. During diastole, where blood flows from the left atrium 102 towards the left ventricle 104, the flap 50 can transition from the expanded state back to the collapsed state.

In some situations such as those shown in FIGS. 13A and 14A, the annular flap 50 may not contact the wall of the heart 100. This may occur when the annular flap 50 is in a collapsed configuration although it may also occur when the annular flap 50 is in an expanded configuration. In some situations such as those shown in FIGS. 13B, 13C and 14B, the annular flap 50 may contact the wall of the heart 100. This may occur when the annular flap 50 is in an expanded configuration although it may also occur when the annular flap 50 is in a collapsed configuration. As shown in FIG. 13A-14B, the annular flap 50 can also assist in filling gaps which exist between the leaflet 108 and the frame 20 (portions of which are illustrated in dashed lines).

In some situations such as that shown in FIG. 15, the leaflet 108 may not be captured between the frame 20 (portions of which are shown in dashed lines) and the distal anchors 30. As shown, the anchor 30 may be positioned along an atrial surface of the leaflet 108. The anchor 30 may also be positioned along an inner surface of the annulus 106. It is also contemplated that the anchor 30 may exert a force against the leaflet 108 such that the leaflet 108 is pushed radially outward, relative to the longitudinal axis 28, towards a wall of the heart 100. In such situations, the flap 50 can create a seal intra-annularly and/or along an atrial side of the leaflet 108. In alternative situations (not shown), the flap 50 can create a seal along a ventricular side of the annulus 106. For example, the replacement heart valve 10 may be disposed in the mitral annulus such that a portion of the annular flap 50 is positioned on the ventricular side of the native annulus 106.

As noted above, although the in vivo situations of FIG. 13A-15 have been described separately, it should be understood that one or more of these situations may be present when a prosthesis is positioned at the implantation location, such as a native mitral valve. For example, one or more of the distal anchors 30 may not capture the leaflet 108 whereas the remaining anchors 30 may capture the leaflet 108. As another example, when the prosthesis 10 is positioned within the native mitral valve, the annular flap 50 can contact the wall of the heart 100 along one or more portions of an outermost circumference of the proximal portion 51 and may not contact the wall of the heart 100 along other portions of the outermost circumference of the proximal portion 51. For example, the annular flap 50 may contact the wall of the heart 100 along an approximately 180 degree portion of the outermost circumference of the proximal portion 51 and may not contact the wall of the heart 100 along the remaining, approximately 180 degree portion of the outermost circumference of the proximal portion 51.

Replacement heart valves can be delivered to a patient's heart mitral valve annulus in various ways, such as by open surgery, minimally-invasive surgery, and percutaneous or transcatheter delivery through the patient's vasculature. In some embodiments, the replacement heart valve can be delivered transapically or transfemorally.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A prosthesis for placement within a native mitral valve having a native mitral valve annulus, the prosthesis comprising:
   an expandable frame comprising a proximal end, a distal end, and a middle region between the proximal end and the distal end, the expandable frame configured to radially expand for deployment within the native mitral valve annulus;
   a plurality of distal anchors connected to the expandable frame and extending from the distal end of the expandable frame, at least a portion of each of the plurality of distal anchors extending generally proximally when the expandable frame is in an expanded configuration, alternating distal anchors of the plurality of distal anchors comprising a cushion on a proximally-extending tip of the distal anchor;

an anchoring structure connected to the expandable frame configured to facilitate anchoring of the expandable frame within the native mitral valve annulus; and a valve body positioned within an interior of the expandable frame;

an inner skirt secured to the interior of the expandable frame, wherein the valve body comprises a plurality of leaflets configured to allow flow in a first direction and prevent flow in a second opposite direction, wherein each leaflet of the plurality of leaflets comprises a proximal edge which is fixed to the inner skirt and a distal edge which freely moves, and wherein, when in the expanded configuration, the middle region of the expandable frame has a different maximum cross-sectional dimension than a maximum cross-sectional dimension of the proximal end and the distal end of the expandable frame.

2. The prosthesis of claim 1, wherein, when in the expanded configuration, a contact portion of the anchoring structure is positioned radially outward from the expandable frame.

3. The prosthesis of claim 1, wherein, when in the expanded configuration, a contact portion of the anchoring structure has a cross-sectional dimension greater than the maximum cross-sectional dimensions of the proximal end and the middle region of the expandable frame.

4. The prosthesis of claim 1, wherein the proximal edge of each leaflet of the plurality of leaflets is curved.

5. The prosthesis of claim 1, wherein the inner skirt comprises a proximal end, the proximal end comprising edges that undulate between upper portions and lower portions.

6. The prosthesis of claim 1, further comprising an annular flap positioned around and secured to an exterior of the expandable frame.

7. The prosthesis of claim 6, wherein a distal end of the inner skirt comprises one or more cutouts configured to allow fluid to collect within a space that is radially inward of the annular flap so as to cause expansion of the annular flap.

8. The prosthesis of claim 1, wherein, when the expandable frame is in the expanded configuration, the middle region has a larger maximum cross-sectional dimension than the maximum cross-sectional dimensions of the proximal end and the distal end.

9. The prosthesis of claim 1, wherein the inner skirt is manufactured from a more rigid material than the plurality of leaflets.

10. A prosthesis for placement within a native heart valve having a native heart valve annulus, the prosthesis comprising:

an expandable frame comprising a proximal end, a distal end, and a middle region between the proximal end and the distal end, the expandable frame configured to radially expand for deployment within the native heart valve;

a plurality of distal anchors connected to the distal end of the expandable frame and extending from the distal end of the expandable frame, at least a portion of each of the plurality of distal anchors extending generally proximally when the expandable frame is in an expanded configuration, alternating distal anchors of the plurality of distal anchors comprising a cushion on a proximally-extending tip of the distal anchor;

a valve body positioned within an interior of the expandable frame, wherein, when in the expanded configuration, the middle region of the expandable frame has a different maximum cross-sectional dimension than a maximum cross-sectional dimension of the proximal end and the distal end of the expandable frame, wherein the valve body comprises a plurality of leaflets configured to allow flow in a first direction and prevent flow in a second opposite direction; and a skirt secured to the interior of the expandable frame, wherein each leaflet of the plurality of leaflets of the valve body is secured to the skirt, wherein each leaflet of the plurality of leaflets comprises a proximal edge which is secured to the skirt and a distal edge which freely moves, wherein the proximal edge of each leaflet of the plurality of leaflets is curved, and wherein there is clearance between the leaflets and the expandable frame.

11. The prosthesis of claim 10, further comprising an anchoring structure connected to the expandable frame configured to facilitate anchoring of the expandable frame within the native heart valve annulus.

12. The prosthesis of claim 11, wherein, when in the expanded configuration, a contact portion of the anchoring structure is positioned radially outward from the expandable frame.

13. The prosthesis of claim 11, wherein, when in the expanded configuration, a contact portion of the anchoring structure has a cross-sectional dimension greater than the maximum cross-sectional dimensions of the proximal end and the middle region of the expandable frame.

14. The prosthesis of claim 10, wherein the skirt comprises a proximal end, the proximal end comprising edges that undulate between upper portions and lower portions.

15. The prosthesis of claim 10, further comprising an annular flap positioned around and secured to an exterior of the expandable frame.

16. The prosthesis of claim 15, wherein a distal end of the inner skirt comprises one or more cutouts configured to allow fluid to collect within a space that is radially inward of the annular flap so as to cause expansion of the annular flap.

17. The prosthesis of claim 10, wherein the inner skirt is manufactured from a more rigid material than the plurality of leaflets.

* * * * *